United States Patent
Martins et al.

(10) Patent No.: US 12,091,664 B2
(45) Date of Patent: Sep. 17, 2024

(54) METHODS FOR PREVENTING GRAFT ISCHEMIA REPERFUSION INJURY DURING EX VIVO MACHINE PERFUSION PRESERVATION

(71) Applicant: UNIVERSITY OF MASSACHUSETTS, Boston, MA (US)

(72) Inventors: Paulo Martins, Shrewsbury, MA (US); Xiaofei E., Westborough, MA (US); Timothy Kowalik, Princeton, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 880 days.

(21) Appl. No.: 16/961,062

(22) PCT Filed: Jan. 11, 2019

(86) PCT No.: PCT/US2019/013174
§ 371 (c)(1),
(2) Date: Jul. 9, 2020

(87) PCT Pub. No.: WO2019/140176
PCT Pub. Date: Jul. 18, 2019

(65) Prior Publication Data
US 2022/0025374 A1  Jan. 27, 2022

Related U.S. Application Data

(60) Provisional application No. 62/616,838, filed on Jan. 12, 2018.

(51) Int. Cl.
| | | |
|---|---|---|
| *C12N 15/113* | (2010.01) | |
| *A61P 1/16* | (2006.01) | |
| *A61P 9/10* | (2006.01) | |

(52) U.S. Cl.
CPC ............ *C12N 15/1135* (2013.01); *A61P 1/16* (2018.01); *A61P 9/10* (2018.01); *C12N 15/1138* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| 8,940,709 B2 | 1/2015 | Kowalik et al. ............ 514/44 A |
| 2005/0119212 A1 | 6/2005 | Haeberli et al. ............ 514/44 A |
| 2008/0311552 A1 | 12/2008 | Min ................................ 435/1.1 |
| 2014/0030231 A1 | 1/2014 | Yarmush et al. ............ 424/93.7 |
| 2014/0256792 A1 | 9/2014 | Ferdinandy et al. ........ 514/44 A |
| 2015/0230453 A1 | 8/2015 | Fontes et al. ................... 435/1.2 |
| 2016/0024507 A1 | 1/2016 | Kowalik et al. .............. 424/450 |
| 2016/0263195 A1 | 9/2016 | Swaminathan et al. | |

FOREIGN PATENT DOCUMENTS

| WO | WO 2005/013886 A2 | 2/2005 |
| WO | WO 2006/035434 A2 | 6/2006 |
| WO | WO 2015/183842 A1 | 3/2015 |

OTHER PUBLICATIONS

Akimoto, et al., "Temperature-Responsive Polymeric Micelles for Optimizing Drug Targeting to Solid Tumors." *J Control Release*, 193:2-8 (2014).
Ballard, et al., "Effect of Temperature on Absorption Rates of Drug Implants." *J Pharm Sci*, 53:424-428 (1964).
Ballard, "Pharmacokinetics and Temperature." *J Pharm Sci*, 63(9):1345-1358 (1974).
Basak and Bandyopadhyay, "Encapsulation of Hydrophobic Drugs in Pluronic F127 Micelles: Effects of Drug Hydrophobicity, Solution Temperature, and pH." *Langmuir*, 29(13):4350-4356 (2013).
Biguzas, et al., "Evaluation of UW Solution in a Rat Kidney Preservation Model. I. Effect of Hydroxyethyl Starch and Electrolyte Composition." *Transplantation*, 49(5):872-875 (1990).
Bradley, et al., "Successful Incorporation of Short-Interfering RNA into Islet Cells by in Situ Perfusion." *Transplantation proceedings*, 37(1):233-236 (2005A).
Bradley, et al., "Gene Silencing in the Endocrine Pancreas Mediated by Short-Interfering RNA." *Pancreas*, 31(4):373-379 (2005B).
Brasile, et al., "Transfection and Transgene Expression in a Human Kidney During Ex Vivo Warm Perfusion." *Transplant Proc*, 34(7):2624 (2002).
Brummelkamp, et al., "A System for Stable Expression of Short Interfering RNAs in Mammalian Cells." *Science*, 296(5567):550-553 (2002).
Cosio, et al., "Impact of Acute Rejection and Early Allograft Function on Renal Allograft Survival." *Transplantation*, 63(11):1611-1615 (1997).
Fuhrman, "The Effect of Body Temperature on Drug Action." *Physiol Rev*, 26:247-274 (1946).
Game and Lechler, "Pathways of Allorecognition: Implications for Transplantation Tolerance." *Transpl Immunol*, 10(2-3):101-108 (2002).
Hackstein and Thomson, "Dendritic Cells: Emerging Pharmacological Targets of Immunosuppressive Drugs." *Nat Rev Immunol*, 4(1):24-34 (2004).
Hart and Fabre, "Antibodies to Liver-Specific Auto- and Alloantigens after Alloimmunization with Liver Tissue in the Rat." *Transplantation*, 31(3):178-182 (1981A).
Hart and Fabre, "Endogenously Produced IA Antigens within Cells of Convoluted Tubules of Rat Kidney." *J Immunol*, 126(6):2109-2113 (1981B).

(Continued)

*Primary Examiner* — Brian Whiteman
(74) *Attorney, Agent, or Firm* — Medlen & Carroll, LLP

(57) ABSTRACT

The invention provides methods for treating ischemia (such as ischemia repertusion injury (IRI)) in tissue (such as transplant donor tissue), comprising contacting the tissue during ex vivo perfusion with a therapeutically effective amount of RNAi (such as siRNA) that specifically hinds to at least a portion of a gene (such as p53) that mediates ischemic injury in the tissue. The invention's methods additionally decrease the risk of tissue rejection and/or or induce immunological tolerance to transplanted tissue.

11 Claims, 13 Drawing Sheets
Specification includes a Sequence Listing.

(56) References Cited

OTHER PUBLICATIONS

Hart and Fabre, "Passive Enhancement of Rat Renal Allografts Using Mouse Monoclonal Xenoantibodies." *Transplantation*, 32(5):431-436 (1981C).

Hart and Fabre, "Antibody Response after Alloimmunization with Heart Tissue in the Rat. Characterization of the Alloantibodies." *Transplantation*, 31(3):174-177 (1981D).

Ibrahim, et al., "Predominant Infiltration of Rejecting Human Renal Allografts with T Cells Expressing CD8 and CD45ro." *Transplantation*, 59(5):724-728 (1995).

Jayaraman, et al., "Maximizing the Potency of siRNA Lipid Nanoparticles for Hepatic Gene Silencing in Vivo." *Angew Chem Int Ed Engl*, 51(34):8529-8533 (2012).

Johnston, et al., "Sensitivity of Expanded-Criteria Donor Kidneys to Cold Ischaemia Time." *Clin Transplant*, 18 Suppl 12:28-32 (2004).

Karmann, et al., "CD40 on Human Endothelial Cells: Inducibility by Cytokines and Functional Regulation of Adhesion Molecule Expression." *Proc Natl Acad Sci U S A*, 92(10):4342-4346 (1995).

Koga, et al., "Inhibition of Acute Graft Rejection in Mice through Neutralization of the Chemokine MIG." *Transplantation*, 67(7):S247 one page (1999).

Lee, et al., "Heat Shock Response, Heat Shock Transcription Factor and Cell Aging." *Biol Signals*, 5(3):180-191 (1996).

Lee, et al., "Expression of Small Interfering RNAs Targeted against HIV-1 Rev Transcripts in Human Cells." *Nat Biotechnol*, 20(5):500-505 (2002).

Leggat, et al., "Long-Term Renal Allograft Survival: Prognostic Implication of the Timing of Acute Rejection Episodes." *Transplantation*, 63(9):1268-1272 (1997).

Mackersie, et al., "Organ Procurement in Patients with Fatal Head Injuries. The Fate of the Potential Donor." *Ann Surg*, 213(2):143-150 (1991).

Magin and Niesman, "Temperature-Dependent Drug Release from Large Unilamellar Liposomes." *Cancer Drug Deliv*, 1(2):109-117 (1984).

Matzinger, "The Danger Model: A Renewed Sense of Self." *Science*, 296(5566):301-305 (2002).

Medzhitov and Janeway, "Innate Immunity: Impact on the Adaptive Immune Response." *Curr Opin Immunol*, 9(1):4-9 (1997).

Miyagishi and Taira, "U6 Promoter-Driven siRNAs with Four Uridine 3' Overhangs Efficiently Suppress Targeted Gene Expression in Mammalian Cells." *Nat Biotechnol*, 20(5):497-500 (2002).

Neff, et al., "The Current Economic Burden of Cirrhosis." *Gastroenterol Hepatol (N Y)*, 7(10):661-671 (2011).

Ojo, et al., "Delayed Graft Function: Risk Factors and Implications for Renal Allograft Survival." *Transplantation*, 63(7):968-974 (1997).

Paddison, et al., "Short Hairpin RNAs (ShRNAs) Induce Sequence-Specific Silencing in Mammalian Cells." *Genes Dev*, 16(8):948-958 (2002).

Paul, et al., "Effective Expression of Small Interfering RNA in Human Cells." *Nat Biotechnol*, 20(5):505-508 (2002).

Pratschke, et al., "Accelerated Rejection of Renal Allografts from Brain-Dead Donors." *Ann Surg*, 232(2):263-271 (2000).

Pratschke, et al., "Brain Death Associated Ischemia/Reperfusion Injury." *Ann Transplant*, 9(1):78-80 (2004).

Raftery, et al., "The Relevance of Induced Class II HLA Antigens and Macrophage Infiltration in Early Renal Allograft Biopsies." *Transplantation*, 48(2):238-243 (1989).

Rosendale, et al., "Increased Transplanted Organs from the Use of a Standardized Donor Management Protocol." *Am J Transplant*, 2(8):761-768 (2002).

Schuurs, et al., "Distinct Transcriptional Changes in Donor Kidneys Upon Brain Death Induction in Rats: Insights in the Processes of Brain Death." *Am J Transplant*, 4(12):1972-1981 (2004).

Southard and Belzer, "Organ Preservation." *Annu Rev Med*, 46:235-247 (1995).

Sui, et al., "A DNA Vector-Based RNAi Technology to Suppress Gene Expression in Mammalian Cells." *Proceedings of the National Academy of Sciences of the United States of America*, 99(8):5515-5520 (2002).

Takada, et al., "The Role of the B7 Costimulatory Pathway in Experimental Cold Ischemia/Reperfusion Injury." *J Clin Invest*, 100(5):1199-1203 (1997).

Takeda, et al., "Toll-Like Receptors." *Annu Rev Immunol*, 21:335-376 (2003).

Terasaki, et al., "High Survival Rates of Kidney Transplants from Spousal and Living Unrelated Donors." *N Engl J Med*, 333(6):333-336 (1995).

Thijssen, et al., "Silencing P53 Pathway of Apoptosis Alleviates Ischemia-Reperfusion Injury (IRI) in the Liver." *Journal of the American College of Surgeons*, 225(4):e167 one page (2017).

Troppmann, et al., "Delayed Graft Function, Acute Rejection, and Outcome after Cadaver Renal Transplantation. The Multivariate Analysis." *Transplantation*, 59(7):962-968 (1995).

Tullius, et al., "Transplantation of Organs from Marginal Donors." *Transplantation*, 72(8):1341-1349 (2001).

Valero, "Donor Management: One Step Forward." *American Journal of Transplantation*, 2(8):693-694 (2002A).

Valero, et al., "A Defective NF-KAPPA B/RELB Pathway in Autoimmune-Prone New Zealand Black Mice is Associated with Inefficient Expansion of Thymocyte and Dendritic Cells." *J Immunol*, 169(1):185-192 (2002B).

Van der Woude, "Graft Immunogenicity Revisited: Relevance of Tissue-Specific Immunity, Brain Death and Donor Pretreatment." *Nephron*, 91(2):181-187 (2002).

Volpe, et al., "Effect of Altered Temperature Storage on the in Vitro Cellular Uptake of Liposome Drug Products." *J Liposome Res*, 20(2):178-182 (2010).

Wood, "Passenger Leukocytes and Microchimerism: What Role in Tolerance Induction?". *Transplantation*, 75(9 Suppl):17S-20S (2003).

Ying, et al., "Targeted Deletion of P53 in the Proximal Tubule Prevents Ischemic Renal Injury." *J Am Soc Nephrol*, 25(12):2707-2716 (2014).

Yu, et al., "RNA Interference by Expression of Short-Interfering RNAs and Hairpin RNAs in Mammalian Cells." *Proceedings of the National Academy of Sciences*, 99(9):6047-6052 (2002).

Thijssen, et al., "Gene Silencing with siRNA (RNA Interference): A New Therapeutic Option During Ex Vivo Machine Liver Perfusion Preservation." *Liver Transplantation : Official Publication of The American Association for The Study of Liver Diseases and The International Liver Transplantation Society*, 25(1):140-151 (2019).

Zheng, et al., "Attenuating Ischemia-Reperfusion Injury in Kidney Transplantation by Perfusing Donor Organs with siRNA Cocktail Solution." *Transplantation*, 100(4):743-752 (2016).

Figure 3 Inflammatory cytokines assessed by Elisa analysis of perfused livers treated with p53 siRNA vs untreated controls.

: Neutrophil infiltration assessed by myeloperoxidase analysis of clamped livers treated with p53 siRNA vs untreated controls.

p53: U94788
1. GCATGAACCGAGGCCCAT (SEQ ID NO: 1)
2. CCACTGGATGGAGAATATT (SEQ ID NO: 22)
3. GCGGAACTCGAATTCATTT (SEQ ID NO: 23)
4. GCTCTTGTCTTTCAGACTT (SEQ ID NO: 24)
5. GCTTTCTCCTGCTGCTTAT (SEQ ID NO: 25)
6. GCCACCATCTTGATTTGAA (SEQ ID NO: 26)

NFKB1: NM_003998
1. GCAGAAGATGATCCATATT (SEQ ID NO: 27)
2. GGATCCTTCTTTGACTCAT (SEQ ID NO: 28)
3. GCTATAATCCTGGACTCTT (SEQ ID NO: 29)
4. CCACCTTCATTCTCAACTT (SEQ ID NO: 30)
5. GGACAGTACTACCTACGAT (SEQ ID NO: 31)

IFN-gamma:X13274
1. GGTTCTCTTGGCTGTTACT (SEQ ID NO: 32)
2. GCAGGTCATTCAGATGTAG (SEQ ID NO: 33)
3. TCATTCAGATGTAGCGGAT (SEQ ID NO: 34)
4. CCAACGCAAAGCAATACAT (SEQ ID NO: 35)
5. GAGTCAGATGCTGTTTCAA (SEQ ID NO: 36)

TNF-alpha: HQ201306
1. GCCTGTAGCCCATGTTGTA (SEQ ID NO: 37)
2. GCGTGGAGCTGAGAGATAA (SEQ ID NO: 38)
3. GCCCGACTATCTCGACTTT (SEQ ID NO: 39)
4. GGCAGGTCTACTTTGGGAT (SEQ ID NO: 40)
5. GGTCTACTTTGGGATCATT (SEQ ID NO: 41)

IL 1: M28983
1. GCCCGGCCTGGAGTTTCTA (SEQ ID NO: 42)
2. CCCGGCCTGGAGTTTCTAC (SEQ ID NO: 43)
3. CCGGCCTGGAGTTTCTACT (SEQ ID NO: 44)
4. GGCCTGGAGTTTCTACTGT (SEQ ID NO: 45)
5. GCCTGGAGTTTCTACTGTG (SEQ ID NO: 46)

IL 2: S77834
1. GCAACTCCTGTCTTGCATT (SEQ ID NO: 47)
2. GCACCTACTTCAAGTTCTA (SEQ ID NO: 48)
3. GGAGCATTTACTGCTGGAT (SEQ ID NO: 49)
4. TCACCAGGATGCTCACATT (SEQ ID NO: 50)
5. CCAGGGACTTAATCAGCAA (SEQ ID NO: 51)

FIG. 7A

IL 6: BC015511
1. GCTGCAGGACATGACAACT (SEQ ID NO: 52)
2. GCAGGACATGACAACTCAT (SEQ ID NO: 53)
3. TCTCATTCTGCGCAGCTTT (SEQ ID NO: 54)
4. TCATTCTGCGCAGCTTTAA (SEQ ID NO: 55)
5. GCAGCTTTAAGGAGTTCCT (SEQ ID NO: 56)

TNF-beta: X02911
1. CCTTGGGCTGCCCGTGCTT (SEQ ID NO: 57)
2. GCCTGGGCTTGGTGGGTT (SEQ ID NO: 58)
3. CCTGGGCCTTGGTGGGTTT (SEQ ID NO: 59)
4. GCCATGGTTCCTCTCTGTT (SEQ ID NO: 60)
5. GGTTCCTCTCTGTTCCCTT (SEQ ID NO: 61)

FAS: KM114217
1. GCAGGCCAAGTTGCTGAAT (SEQ ID NO: 4)
2. GGCCAAGTTGCTGAATCAA (SEQ ID NO: 5)
3. GCCAAGTTGCTGAATCAAT (SEQ ID NO: 6)
4. TCGTGAGCTCGTCTCTGAT (SEQ ID NO: 7)
5. CCCGCGCGCAGGCCAAGTT (SEQ ID NO: 8)

BAX transcript variant 1: NM_001291428
1. GCTCTGAGCAGATCATGAA (SEQ ID NO: 62)
2. GCTTCAGGGTTTCATCCAG (SEQ ID NO: 63)
3. TCAGGGTTTCATCCAGGAT (SEQ ID NO: 64)
4. GGTTTCATCCAGGATCGAG (SEQ ID NO: 65)
5. GGATGCGTCCACCAAGAAG (SEQ ID NO: 66)

Caspase-3 transcript variant 1: NM_004346
1. GGAACCAAAGATCATACAT (SEQ ID NO: 67)
2. GCAAACCTCAGGGAAACAT (SEQ ID NO: 68)
3. GCCGACTTCTTGTATGCAT (SEQ ID NO: 69)
4. GCTTTGTGCCATGCTGAAA (SEQ ID NO: 70)
5. CCGACAAGCTTGAATTTAT (SEQ ID NO: 71)

Caspase-8: AB038985
1. GCAGGAATCATTATAGCTA (SEQ ID NO: 72)
2. GCTACCATCGTGAGAGTAA (SEQ ID NO: 73)
3. GCAAGTAGAATGACGTCTA (SEQ ID NO: 74)
4. GCACGAGATTAAGTCCATT (SEQ ID NO: 75)
5. CCTTATGTCTAGCCCACTT (SEQ ID NO: 76)

FIG. 7B

C5a: M59863
1. GGCTGGTTTCGCTACCGTT (SEQ ID NO: 77)
2. GCTGGTTTCGCTACCGTTG (SEQ ID NO: 78)
3. GCAAGCTGACTACAAGGAC (SEQ ID NO: 79)
4. GCTGACTACAAGGACGACG (SEQ ID NO: 80)
5. GGACGACGATGACAAGCTT (SEQ ID NO: 81)

C3: K02765
1. GGACGGTCATGGTCAACAT (SEQ ID NO: 82)
2. GGGAAGAAAGTGGAGGGAA (SEQ ID NO: 83)
3. CCTCAAGCGCATTCCGATT (SEQ ID NO: 84)
4. CCACCAACCACATGGGCAA (SEQ ID NO: 85)
5. GGACCCAAGTGGTGGAGAA (SEQ ID NO: 86)

MHC class II DN alpha: M26039
1. GCGCCACTCCTCAGGCATT (SEQ ID NO: 87)
2. GCATCGTGGACAACATCTT (SEQ ID NO: 88)
3. GCCTATTCCACCACCAGAT (SEQ ID NO: 89)
4. GGGAGCTCCAGGTGCCTAT (SEQ ID NO: 90)
5. GGAGCTCCAGGTGCCTATT (SEQ ID NO: 91)

TLR4: U88880
1. GATTTATCCAGGTGTGAA (SEQ ID NO: 92)
2. CTCACAATCTTATCCAAT (SEQ ID NO: 93)
3. CTGAACCCTATGAACTTT (SEQ ID NO: 94)
4. CCTGGTGAGTGTGACTATT (SEQ ID NO: 95)
5. CTGGTGTATCTTTGAATA (SEQ ID NO: 96)

TLR6: BC111755
1. GGTGCTTACAACTGACTAA (SEQ ID NO: 97)
2. GCTTACAACTGACTAATAT (SEQ ID NO: 98)
3. GCATCTAAGTTATATCCTT (SEQ ID NO: 99)
4. CCTTCTGGATTTAAGAAAT (SEQ ID NO: 100)
5. GCTATCCAAGTGAACATAT (SEQ ID NO: 101)

UVRAG: AB012958
1. GCTGAATGATGGATACTAT (SEQ ID NO: 102)
2. GCAGTTACTCTCTGAGCTT (SEQ ID NO: 103)
3. GCTGTTGCCCTTGGTTATA (SEQ ID NO: 104)
4. CCCTGTTCCTAAGAGACAA (SEQ ID NO: 105)
5. CCCAGTTACAACTCAGCAT (SEQ ID NO: 106)

FIG. 7C

ATG3: NM_022488
1. GGAAGAAGATGAAGATGAA (SEQ ID NO: 107)
2. GCTGCAGATATGGAAGAAT (SEQ ID NO: 108)
3. GCAGATATGGAAGAATATG (SEQ ID NO: 109)
4. GAATATGAAGAGAGTGGAT (SEQ ID NO: 110)
5. GGAAGAATATGAAGAGAGT (SEQ ID NO: 111)

Beclin 1: NM_003766
1. GGTCTAAGACGTCCAACAA (SEQ ID NO: 112)
2. GGACAACAAGTTTGACCAT (SEQ ID NO: 113)
3. GCACCATGCAGGTGAGCTT (SEQ ID NO: 114)
4. GGGCCAGACAGATGTGGAT (SEQ ID NO: 115)
5. GCTCAGTATCAGAGAGAAT (SEQ ID NO: 116)

FIG. 7D

SEQUENCE LISTING

<160> NUMBER OF SEQ ID NOS: 116

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
gcatgaaccg aggcccat                                          18

<210> SEQ ID NO 2
<211> LENGTH: 18
<212> TYPE: DNA
<213> ORGANISM: Artificial Sequence

```
<220> FEATURE:
<223> OTHER INFORMATION: Synthetic

<400> SEQUENCE: 2
gcaugaaccg aggcccau                                                    18

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
augggccucg guucaugc                                                    18

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
gcaggccaag ttgctgaat                                                   19

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
ggccaagttg ctgaatcaa                                                   19

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
gccaagttgc tgaatcaat                                                   19

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
tcgtgagctc gtctctgat                                                   19

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
cccgcgcgca ggccaagtt                                                   19
```

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
gugcaagugc aaaccagacd tdt                                              23

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
agccgaaugu cgcagaaccd tdt                                              23

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11
ggauuauauc aaggaggccd tdt                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12
aucgccuaug guuguugacd tdt                                              23

<210> SEQ ID NO 13
<211> LENGTH: 23
<212> TYPE: DNA
<213> ORGANISM: Artificial Sequence
<220> FEATURE:
<223> OTHER INFORMATION: Synthetic

<400> SEQUENCE: 13
auacaucccg agaauugcud tdt                                              23

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
aagccgaaug ucgcagaacd tdt                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic

```
<400> SEQUENCE: 15
gucugguuug cacuugcacd tdt                                    23

<210> SEQ ID NO 16
<211> LENGTH: 23
<212> TYPE: DNA
<213> ORGANISM: Artificial Sequence
<220> FEATURE:
<223> OTHER INFORMATION: Synthetic

<400> SEQUENCE: 16
ggccuccuug auauaauccd tdt                                    23

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
gucaacaacc auaggcgaud tdt                                    23

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
agcaauucuc gggauguaud tdt                                    23

<210> SEQ ID NO 19
<211> LENGTH: 23
<212> TYPE: DNA
<213> ORGANISM: Artificial Sequence
<220> FEATURE:
<223> OTHER INFORMATION: Synthetic

<400> SEQUENCE: 19
guucugcgac auucggcuud tdt                                    23

<210> SEQ ID NO 20
<211> LENGTH: 25
<212> TYPE: DNA
<213> ORGANISM: Artificial Sequence
<220> FEATURE:
<223> OTHER INFORMATION: Synthetic

<400> SEQUENCE: 20
gucugguuug cacuugcacd tdtcy                                  25

<210> SEQ ID NO 21
<211> LENGTH: 22
<212> TYPE: DNA
<213> ORGANISM: Artificial Sequence
<220> FEATURE:
<223> OTHER INFORMATION: Synthetic

<400> SEQUENCE: 21
guucugcgac auucggcudt dt                                     22

<210> SEQ ID NO 22
```

```
<211> LENGTH: 19
<212> TYPE: DNA
<213> ORGANISM: Artificial Sequence
<220> FEATURE:
<223> OTHER INFORMATION: Synthetic

<400> SEQUENCE: 22
ccactggatg gagaatatt                                                    19

<210> SEQ ID NO 23
<211> LENGTH: 19
<212> TYPE: DNA
<213> ORGANISM: Artificial Sequence
<220> FEATURE:
<223> OTHER INFORMATION: Synthetic

<400> SEQUENCE: 23
gcggaactcg aattcattt                                                    19

<210> SEQ ID NO 24
<211> LENGTH: 19
<212> TYPE: DNA
<213> ORGANISM: Artificial Sequence
<220> FEATURE:
<223> OTHER INFORMATION: Synthetic

<400> SEQUENCE: 24
gctcttgtct ttcagactt                                                    19

<210> SEQ ID NO 25
<211> LENGTH: 19
<212> TYPE: DNA
<213> ORGANISM: Artificial Sequence
<220> FEATURE:
<223> OTHER INFORMATION: Synthetic

<400> SEQUENCE: 25
gctttctcct gctgcttat                                                    19

<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26
gccaccatct tgatttgaa                                                    19

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
gcagaagatg atccatatt                                                    19

<210> SEQ ID NO 28
<211> LENGTH: 19
<212> TYPE: DNA
<213> ORGANISM: Artificial Sequence
<220> FEATURE:
<223> OTHER INFORMATION: Synthetic

<400> SEQUENCE: 28
```
ggatccttct ttgactcat                                                19

<210> SEQ ID NO 29
<211> LENGTH: 19
<212> TYPE: DNA
<213> ORGANISM: Artificial Sequence
<220> FEATURE:
<223> OTHER INFORMATION: Synthetic

<400> SEQUENCE: 29
gctataatcc tggactctt                                                19

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
ccaccttcat tctcaactt                                                19

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
ggacagtact acctacgat                                                19

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
ggttctcttg gctgttact                                                19

<210> SEQ ID NO 33
<211> LENGTH: 19
<212> TYPE: DNA
<213> ORGANISM: Artificial Sequence
<220> FEATURE:
<223> OTHER INFORMATION: Synthetic

<400> SEQUENCE: 33
gcaggtcatt cagatgtag                                                19

<210> SEQ ID NO 34
<211> LENGTH: 19
<212> TYPE: DNA
<213> ORGANISM: Artificial Sequence
<220> FEATURE:
<223> OTHER INFORMATION: Synthetic

<400> SEQUENCE: 34
tcattcagat gtagcggat                                                19

<210> SEQ ID NO 35
<211> LENGTH: 19
<212> TYPE: DNA

<213> ORGANISM: Artificial Sequence
<220> FEATURE:
<223> OTHER INFORMATION: Synthetic

<400> SEQUENCE: 35
ccaacgcaaa gcaatacat       19

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
gagtcagatg ctgtttcaa       19

<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37
gcctgtagcc catgttgta       19

<210> SEQ ID NO 38
<211> LENGTH: 19
<212> TYPE: DNA
<213> ORGANISM: Artificial Sequence
<220> FEATURE:
<223> OTHER INFORMATION: Synthetic

<400> SEQUENCE: 38
gcgtggagct gagagataa       19

<210> SEQ ID NO 39
<211> LENGTH: 19
<212> TYPE: DNA
<213> ORGANISM: Artificial Sequence
<220> FEATURE:
<223> OTHER INFORMATION: Synthetic

<400> SEQUENCE: 39
gcccgactat ctcgacttt       19

<210> SEQ ID NO 40
<211> LENGTH: 19
<212> TYPE: DNA
<213> ORGANISM: Artificial Sequence
<220> FEATURE:
<223> OTHER INFORMATION: Synthetic

<400> SEQUENCE: 40
ggcaggtcta ctttgggat       19

<210> SEQ ID NO 41
<211> LENGTH: 19
<212> TYPE: DNA
<213> ORGANISM: Artificial Sequence
<220> FEATURE:
<223> OTHER INFORMATION: Synthetic

<400> SEQUENCE: 41
ggtctacttt gggatcatt       19

<210> SEQ ID NO 42
<211> LENGTH: 19
<212> TYPE: DNA
<213> ORGANISM: Artificial Sequence
<220> FEATURE:
<223> OTHER INFORMATION: Synthetic

<400> SEQUENCE: 42
gcccggcctg gagtttcta                                              19

<210> SEQ ID NO 43
<211> LENGTH: 19
<212> TYPE: DNA
<213> ORGANISM: Artificial Sequence
<220> FEATURE:
<223> OTHER INFORMATION: Synthetic

<400> SEQUENCE: 43
cccggcctgg agtttctac                                              19

<210> SEQ ID NO 44
<211> LENGTH: 19
<212> TYPE: DNA
<213> ORGANISM: Artificial Sequence
<220> FEATURE:
<223> OTHER INFORMATION: Synthetic

<400> SEQUENCE: 44
ccggcctgga gtttctact                                              19

<210> SEQ ID NO 45
<211> LENGTH: 19
<212> TYPE: DNA
<213> ORGANISM: Artificial Sequence
<220> FEATURE:
<223> OTHER INFORMATION: Synthetic

<400> SEQUENCE: 45
ggcctggagt ttctactgt                                              19

<210> SEQ ID NO 46
<211> LENGTH: 19
<212> TYPE: DNA
<213> ORGANISM: Artificial Sequence
<220> FEATURE:
<223> OTHER INFORMATION: Synthetic

<400> SEQUENCE: 46
gcctggagtt tctactgtg                                              19

<210> SEQ ID NO 47
<211> LENGTH: 19
<212> TYPE: DNA
<213> ORGANISM: Artificial Sequence
<220> FEATURE:
<223> OTHER INFORMATION: Synthetic

<400> SEQUENCE: 47
gcaactcctg tcttgcatt                                              19

<210> SEQ ID NO 48
<211> LENGTH: 19
<212> TYPE: DNA
<213> ORGANISM: Artificial Sequence
<220> FEATURE:

<223> OTHER INFORMATION: Synthetic

<400> SEQUENCE: 48
gcacctactt caagttcta                                            19

<210> SEQ ID NO 49
<211> LENGTH: 19
<212> TYPE: DNA
<213> ORGANISM: Artificial Sequence
<220> FEATURE:
<223> OTHER INFORMATION: Synthetic

<400> SEQUENCE: 49
ggagcattta ctgctggat                                            19

<210> SEQ ID NO 50
<211> LENGTH: 19
<212> TYPE: DNA
<213> ORGANISM: Artificial Sequence
<220> FEATURE:
<223> OTHER INFORMATION: Synthetic

<400> SEQUENCE: 50
tcaccaggat gctcacatt                                            19

<210> SEQ ID NO 51
<211> LENGTH: 19
<212> TYPE: DNA
<213> ORGANISM: Artificial Sequence
<220> FEATURE:
<223> OTHER INFORMATION: Synthetic

<400> SEQUENCE: 51
ccagggactt aatcagcaa                                            19

<210> SEQ ID NO 52
<211> LENGTH: 19
<212> TYPE: DNA
<213> ORGANISM: Artificial Sequence
<220> FEATURE:
<223> OTHER INFORMATION: Synthetic

<400> SEQUENCE: 52
gctgcaggac atgacaact                                            19

<210> SEQ ID NO 53
<211> LENGTH: 19
<212> TYPE: DNA
<213> ORGANISM: Artificial Sequence
<220> FEATURE:
<223> OTHER INFORMATION: Synthetic

<400> SEQUENCE: 53
gcaggacatg acaactcat                                            19

<210> SEQ ID NO 54
<211> LENGTH: 19
<212> TYPE: DNA
<213> ORGANISM: Artificial Sequence
<220> FEATURE:
<223> OTHER INFORMATION: Synthetic

<400> SEQUENCE: 54
tctcattctg cgcagcttt                                            19

<210> SEQ ID NO 55
<211> LENGTH: 19
<212> TYPE: DNA
<213> ORGANISM: Artificial Sequence
<220> FEATURE:
<223> OTHER INFORMATION: Synthetic

<400> SEQUENCE: 55
tcattctgcg cagctttaa                                              19

<210> SEQ ID NO 56
<211> LENGTH: 19
<212> TYPE: DNA
<213> ORGANISM: Artificial Sequence
<220> FEATURE:
<223> OTHER INFORMATION: Synthetic

<400> SEQUENCE: 56
gcagctttaa ggagttcct                                              19

<210> SEQ ID NO 57
<211> LENGTH: 19
<212> TYPE: DNA
<213> ORGANISM: Artificial Sequence
<220> FEATURE:
<223> OTHER INFORMATION: Synthetic

<400> SEQUENCE: 57
ccttgggctg cccgtgctt                                              19

<210> SEQ ID NO 58
<211> LENGTH: 19
<212> TYPE: DNA
<213> ORGANISM: Artificial Sequence
<220> FEATURE:
<223> OTHER INFORMATION: Synthetic

<400> SEQUENCE: 58
gcctgggcct tggtgggtt                                              19

<210> SEQ ID NO 59
<211> LENGTH: 19
<212> TYPE: DNA
<213> ORGANISM: Artificial Sequence
<220> FEATURE:
<223> OTHER INFORMATION: Synthetic

<400> SEQUENCE: 59
cctgggcctt ggtgggttt                                              19

<210> SEQ ID NO 60
<211> LENGTH: 19
<212> TYPE: DNA
<213> ORGANISM: Artificial Sequence
<220> FEATURE:
<223> OTHER INFORMATION: Synthetic

<400> SEQUENCE: 60
gccatggttc ctctctgtt                                              19

<210> SEQ ID NO 61
<211> LENGTH: 19
<212> TYPE: DNA
<213> ORGANISM: Artificial Sequence
<220> FEATURE:
<223> OTHER INFORMATION: Synthetic

```
<400> SEQUENCE: 61
ggttcctctc tgttccctt                                               19

<210> SEQ ID NO 62
<211> LENGTH: 19
<212> TYPE: DNA
<213> ORGANISM: Artificial Sequence
<220> FEATURE:
<223> OTHER INFORMATION: Synthetic

<400> SEQUENCE: 62
gctctgagca gatcatgaa                                               19

<210> SEQ ID NO 63
<211> LENGTH: 19
<212> TYPE: DNA
<213> ORGANISM: Artificial Sequence
<220> FEATURE:
<223> OTHER INFORMATION: Synthetic

<400> SEQUENCE: 63
gcttcagggt ttcatccag                                               19

<210> SEQ ID NO 64
<211> LENGTH: 19
<212> TYPE: DNA
<213> ORGANISM: Artificial Sequence
<220> FEATURE:
<223> OTHER INFORMATION: Synthetic

<400> SEQUENCE: 64
tcagggtttc atccaggat                                               19

<210> SEQ ID NO 65
<211> LENGTH: 19
<212> TYPE: DNA
<213> ORGANISM: Artificial Sequence
<220> FEATURE:
<223> OTHER INFORMATION: Synthetic

<400> SEQUENCE: 65
ggtttcatcc aggatcgag                                               19

<210> SEQ ID NO 66
<211> LENGTH: 19
<212> TYPE: DNA
<213> ORGANISM: Artificial Sequence
<220> FEATURE:
<223> OTHER INFORMATION: Synthetic

<400> SEQUENCE: 66
ggatgcgtcc accaagaag                                               19

<210> SEQ ID NO 67
<211> LENGTH: 19
<212> TYPE: DNA
<213> ORGANISM: Artificial Sequence
<220> FEATURE:
<223> OTHER INFORMATION: Synthetic

<400> SEQUENCE: 67
ggaaccaaag atcatacat                                               19

<210> SEQ ID NO 68
<211> LENGTH: 19
```

<212> TYPE: DNA
<213> ORGANISM: Artificial Sequence
<220> FEATURE:
<223> OTHER INFORMATION: Synthetic

<400> SEQUENCE: 68
gcaaacctca gggaaacat                                             19

<210> SEQ ID NO 69
<211> LENGTH: 19
<212> TYPE: DNA
<213> ORGANISM: Artificial Sequence
<220> FEATURE:
<223> OTHER INFORMATION: Synthetic

<400> SEQUENCE: 69
gccgacttct tgtatgcat                                             19

<210> SEQ ID NO 70
<211> LENGTH: 19
<212> TYPE: DNA
<213> ORGANISM: Artificial Sequence
<220> FEATURE:
<223> OTHER INFORMATION: Synthetic

<400> SEQUENCE: 70
gctttgtgcc atgctgaaa                                             19

<210> SEQ ID NO 71
<211> LENGTH: 19
<212> TYPE: DNA
<213> ORGANISM: Artificial Sequence
<220> FEATURE:
<223> OTHER INFORMATION: Synthetic

<400> SEQUENCE: 71
ccgacaagct tgaatttat                                             19

<210> SEQ ID NO 72
<211> LENGTH: 19
<212> TYPE: DNA
<213> ORGANISM: Artificial Sequence
<220> FEATURE:
<223> OTHER INFORMATION: Synthetic

<400> SEQUENCE: 72
gcaggaatca ttatagcta                                             19

<210> SEQ ID NO 73
<211> LENGTH: 19
<212> TYPE: DNA
<213> ORGANISM: Artificial Sequence
<220> FEATURE:
<223> OTHER INFORMATION: Synthetic

<400> SEQUENCE: 73
gctaccatcg tgagagtaa                                             19

<210> SEQ ID NO 74
<211> LENGTH: 19
<212> TYPE: DNA
<213> ORGANISM: Artificial Sequence
<220> FEATURE:
<223> OTHER INFORMATION: Synthetic

<400> SEQUENCE: 74

-continued gcaagtagaa tgacgtcta                                               19

<210> SEQ ID NO 75
<211> LENGTH: 19
<212> TYPE: DNA
<213> ORGANISM: Artificial Sequence
<220> FEATURE:
<223> OTHER INFORMATION: Synthetic

<400> SEQUENCE: 75
gcacgagatt aagtccatt                                               19

<210> SEQ ID NO 76
<211> LENGTH: 19
<212> TYPE: DNA
<213> ORGANISM: Artificial Sequence
<220> FEATURE:
<223> OTHER INFORMATION: Synthetic

<400> SEQUENCE: 76
ccttatgtct agcccactt                                               19

<210> SEQ ID NO 77
<211> LENGTH: 19
<212> TYPE: DNA
<213> ORGANISM: Artificial Sequence
<220> FEATURE:
<223> OTHER INFORMATION: Synthetic

<400> SEQUENCE: 77
ggctggtttc gctaccgtt                                               19

<210> SEQ ID NO 78
<211> LENGTH: 19
<212> TYPE: DNA
<213> ORGANISM: Artificial Sequence
<220> FEATURE:
<223> OTHER INFORMATION: Synthetic

<400> SEQUENCE: 78
gctggtttcg ctaccgttg                                               19

<210> SEQ ID NO 79
<211> LENGTH: 19
<212> TYPE: DNA
<213> ORGANISM: Artificial Sequence
<220> FEATURE:
<223> OTHER INFORMATION: Synthetic

<400> SEQUENCE: 79
gcaagctgac tacaaggac                                               19

<210> SEQ ID NO 80
<211> LENGTH: 19
<212> TYPE: DNA
<213> ORGANISM: Artificial Sequence
<220> FEATURE:
<223> OTHER INFORMATION: Synthetic

<400> SEQUENCE: 80
gctgactaca aggacgacg                                               19

<210> SEQ ID NO 81
<211> LENGTH: 19
<212> TYPE: DNA
<213> ORGANISM: Artificial Sequence
<220> FEATURE:
<223> OTHER INFORMATION: Synthetic

<400> SEQUENCE: 81
ggacgacgat gacaagctt                                            19

<210> SEQ ID NO 82
<211> LENGTH: 19
<212> TYPE: DNA
<213> ORGANISM: Artificial Sequence
<220> FEATURE:
<223> OTHER INFORMATION: Synthetic

<400> SEQUENCE: 82
ggacggtcat ggtcaacat                                            19

<210> SEQ ID NO 83
<211> LENGTH: 19
<212> TYPE: DNA
<213> ORGANISM: Artificial Sequence
<220> FEATURE:
<223> OTHER INFORMATION: Synthetic

<400> SEQUENCE: 83
gggaagaaag tggagggaa                                            19

<210> SEQ ID NO 84
<211> LENGTH: 19
<212> TYPE: DNA
<213> ORGANISM: Artificial Sequence
<220> FEATURE:
<223> OTHER INFORMATION: Synthetic

<400> SEQUENCE: 84
cctcaagcgc attccgatt                                            19

<210> SEQ ID NO 85
<211> LENGTH: 19
<212> TYPE: DNA
<213> ORGANISM: Artificial Sequence
<220> FEATURE:
<223> OTHER INFORMATION: Synthetic

<400> SEQUENCE: 85
ccaccaacca catgggcaa                                            19

<210> SEQ ID NO 86
<211> LENGTH: 19
<212> TYPE: DNA
<213> ORGANISM: Artificial Sequence
<220> FEATURE:
<223> OTHER INFORMATION: Synthetic

<400> SEQUENCE: 86
ggacccaagt ggtggagaa                                            19

<210> SEQ ID NO 87
<211> LENGTH: 19
<212> TYPE: DNA
<213> ORGANISM: Artificial Sequence
<220> FEATURE:
<223> OTHER INFORMATION: Synthetic

<400> SEQUENCE: 87
gcgccactcc tcaggcatt                                            19

```
<210> SEQ ID NO 88
<211> LENGTH: 19
<212> TYPE: DNA
<213> ORGANISM: Artificial Sequence
<220> FEATURE:
<223> OTHER INFORMATION: Synthetic

<400> SEQUENCE: 88
gcatcgtgga caacatctt                                                    19

<210> SEQ ID NO 89
<211> LENGTH: 19
<212> TYPE: DNA
<213> ORGANISM: Artificial Sequence
<220> FEATURE:
<223> OTHER INFORMATION: Synthetic

<400> SEQUENCE: 89
gcctattcca ccaccagat                                                    19

<210> SEQ ID NO 90
<211> LENGTH: 19
<212> TYPE: DNA
<213> ORGANISM: Artificial Sequence
<220> FEATURE:
<223> OTHER INFORMATION: Synthetic

<400> SEQUENCE: 90
gggagctcca ggtgcctat                                                    19

<210> SEQ ID NO 91
<211> LENGTH: 19
<212> TYPE: DNA
<213> ORGANISM: Artificial Sequence
<220> FEATURE:
<223> OTHER INFORMATION: Synthetic

<400> SEQUENCE: 91
ggagctccag gtgcctatt                                                    19

<210> SEQ ID NO 92
<211> LENGTH: 18
<212> TYPE: DNA
<213> ORGANISM: Artificial Sequence
<220> FEATURE:
<223> OTHER INFORMATION: Synthetic

<400> SEQUENCE: 92
gatttatcca ggtgtgaa                                                     18

<210> SEQ ID NO 93
<211> LENGTH: 18
<212> TYPE: DNA
<213> ORGANISM: Artificial Sequence
<220> FEATURE:
<223> OTHER INFORMATION: Synthetic

<400> SEQUENCE: 93
ctcacaatct tatccaat                                                     18

<210> SEQ ID NO 94
<211> LENGTH: 18
<212> TYPE: DNA
<213> ORGANISM: Artificial Sequence
<220> FEATURE:
<223> OTHER INFORMATION: Synthetic
```

-continued

<400> SEQUENCE: 94 ctgaaccta tgaactttt                                                 18

<210> SEQ ID NO 95
<211> LENGTH: 19
<212> TYPE: DNA
<213> ORGANISM: Artificial Sequence
<220> FEATURE:
<223> OTHER INFORMATION: Synthetic

<400> SEQUENCE: 95
cctggtgagt gtgactatt                                                19

<210> SEQ ID NO 96
<211> LENGTH: 18
<212> TYPE: DNA
<213> ORGANISM: Artificial Sequence
<220> FEATURE:
<223> OTHER INFORMATION: Synthetic

<400> SEQUENCE: 96
ctggtgtatc tttgaata                                                 18

<210> SEQ ID NO 97
<211> LENGTH: 19
<212> TYPE: DNA
<213> ORGANISM: Artificial Sequence
<220> FEATURE:
<223> OTHER INFORMATION: Synthetic

<400> SEQUENCE: 97
ggtgcttaca actgactaa                                                19

<210> SEQ ID NO 98
<211> LENGTH: 19
<212> TYPE: DNA
<213> ORGANISM: Artificial Sequence
<220> FEATURE:
<223> OTHER INFORMATION: Synthetic

<400> SEQUENCE: 98
gcttacaact gactaatat                                                19

<210> SEQ ID NO 99
<211> LENGTH: 19
<212> TYPE: DNA
<213> ORGANISM: Artificial Sequence
<220> FEATURE:
<223> OTHER INFORMATION: Synthetic

<400> SEQUENCE: 99
gcatctaagt tatatcctt                                                19

<210> SEQ ID NO 100
<211> LENGTH: 19
<212> TYPE: DNA
<213> ORGANISM: Artificial Sequence
<220> FEATURE:
<223> OTHER INFORMATION: Synthetic

<400> SEQUENCE: 100
gcatctaagt tatatccttt                                               19

<210> SEQ ID NO 101

```
<211> LENGTH: 19
<212> TYPE: DNA
<213> ORGANISM: Artificial Sequence
<220> FEATURE:
<223> OTHER INFORMATION: Synthetic

<400> SEQUENCE: 101
gctatccaag tgaacatat                                                    19

<210> SEQ ID NO 102
<211> LENGTH: 19
<212> TYPE: DNA
<213> ORGANISM: Artificial Sequence
<220> FEATURE:
<223> OTHER INFORMATION: Synthetic

<400> SEQUENCE: 102
gctgaatgat ggatactat                                                    19

<210> SEQ ID NO 103
<211> LENGTH: 19
<212> TYPE: DNA
<213> ORGANISM: Artificial Sequence
<220> FEATURE:
<223> OTHER INFORMATION: Synthetic

<400> SEQUENCE: 103
gcagttactc tctgagctt                                                    19

<210> SEQ ID NO 104
<211> LENGTH: 19
<212> TYPE: DNA
<213> ORGANISM: Artificial Sequence
<220> FEATURE:
<223> OTHER INFORMATION: Synthetic

<400> SEQUENCE: 104
gctgttgccc ttggttata                                                    19

<210> SEQ ID NO 105
<211> LENGTH: 19
<212> TYPE: DNA
<213> ORGANISM: Artificial Sequence
<220> FEATURE:
<223> OTHER INFORMATION: Synthetic

<400> SEQUENCE: 105
ccctgttcct aagagacaa                                                    19

<210> SEQ ID NO 106
<211> LENGTH: 19
<212> TYPE: DNA
<213> ORGANISM: Artificial Sequence
<220> FEATURE:
<223> OTHER INFORMATION: Synthetic

<400> SEQUENCE: 106
cccagttaca actcagcat                                                    19

<210> SEQ ID NO 107
<211> LENGTH: 19
<212> TYPE: DNA
<213> ORGANISM: Artificial Sequence
<220> FEATURE:
<223> OTHER INFORMATION: Synthetic

<400> SEQUENCE: 107
```
ggaagaagat gaagatgaa                                                19

<210> SEQ ID NO 108
<211> LENGTH: 19
<212> TYPE: DNA
<213> ORGANISM: Artificial Sequence
<220> FEATURE:
<223> OTHER INFORMATION: Synthetic

<400> SEQUENCE: 108
gctgcagata tggaagaat                                                19

<210> SEQ ID NO 109
<211> LENGTH: 19
<212> TYPE: DNA
<213> ORGANISM: Artificial Sequence
<220> FEATURE:
<223> OTHER INFORMATION: Synthetic

<400> SEQUENCE: 109
gcagatatgg aagaatatg                                                19

<210> SEQ ID NO 110
<211> LENGTH: 19
<212> TYPE: DNA
<213> ORGANISM: Artificial Sequence
<220> FEATURE:
<223> OTHER INFORMATION: Synthetic

<400> SEQUENCE: 110
gaatatgaag agagtggat                                                19

<210> SEQ ID NO 111
<211> LENGTH: 19
<212> TYPE: DNA
<213> ORGANISM: Artificial Sequence
<220> FEATURE:
<223> OTHER INFORMATION: Synthetic

<400> SEQUENCE: 111
ggaagaatat gaagagagt                                                19

<210> SEQ ID NO 112
<211> LENGTH: 19
<212> TYPE: DNA
<213> ORGANISM: Artificial Sequence
<220> FEATURE:
<223> OTHER INFORMATION: Synthetic

<400> SEQUENCE: 112
ggtctaagac gtccaacaa                                                19

<210> SEQ ID NO 113
<211> LENGTH: 19
<212> TYPE: DNA
<213> ORGANISM: Artificial Sequence
<220> FEATURE:
<223> OTHER INFORMATION: Synthetic

<400> SEQUENCE: 113
ggacaacaag tttgaccat                                                19

<210> SEQ ID NO 114
<211> LENGTH: 19
<212> TYPE: DNA

```
<213> ORGANISM: Artificial Sequence
<220> FEATURE:
<223> OTHER INFORMATION: Synthetic

<400> SEQUENCE: 114
gcaccatgca ggtgagctt                                                    19

<210> SEQ ID NO 115
<211> LENGTH: 19
<212> TYPE: DNA
<213> ORGANISM: Artificial Sequence
<220> FEATURE:
<223> OTHER INFORMATION: Synthetic

<400> SEQUENCE: 115
gggccagaca gatgtggat                                                    19

<210> SEQ ID NO 116
<211> LENGTH: 19
<212> TYPE: DNA
<213> ORGANISM: Artificial Sequence
<220> FEATURE:
<223> OTHER INFORMATION: Synthetic

<400> SEQUENCE: 116
gctcagtatc agagagaat                                                    19
```

METHODS FOR PREVENTING GRAFT ISCHEMIA REPERFUSION INJURY DURING EX VIVO MACHINE PERFUSION PRESERVATION

This application claims priority to co-pending U.S. provisional Application Ser. No. 62/616,838, filed Jan. 12, 2018, herein incorporated by reference.

A sequence listing has been submitted in an ASCII text filed named "19243", created on Oct. 14, 2021, consisting of 21,493 bytes, the entire content of which is herein incorporated by reference.

FIELD OF THE INVENTION

The invention relates to methods for treating ischemia (such as ischemia reperfusion injury (IRI)) in tissue (such as transplant donor tissue), comprising contacting the tissue during ex vivo perfusion with a therapeutically effective amount of siRNA that specifically binds to at least a portion of a gene (such as p53) that mediates ischemic injury in the tissue. The invention's methods additionally decrease the risk of tissue rejection and/or or induce immunological tolerance to transplanted tissue.

SUMMARY OF THE INVENTION

The invention provides a method for treating ischemia in a target tissue, comprising contacting the tissue, during ex vivo perfusion of the tissue, with a therapeutically effective amount of RNAi sequence (such as siRNA) that specifically binds to at least a portion of a gene that mediates ischemic injury in the tissue, thereby producing a treated tissue. In one embodiment, one or both of the target tissue and the treated tissue is disconnected from a mammalian subject's circulatory system. In another embodiment, the contacting is prior to transplanting the treated tissue to a mammalian recipient. In a further embodiment, the method further comprises the step of transplanting the treated tissue into a transplant recipient. While not intending to limit the type of ischemic injury, the ischemic injury comprises apoptosis and/or inflammation and/or neutrophil infiltration. Without limiting the type of gene that mediates ischemic injury, in one embodiment, the gene is exemplified by one or more of apoptotic gene, inflammatory gene, complement gene, major complex antigen gene, autophagy gene, and Toll like receptor gene. Exemplary genes that mediate ischemic injury include, without limitation, one or more of p53 (U94788), NEKB1 (NM_003998), UN-gamma (X13274), TNF-alpha (HQ201306), IL 1 (M28983), IL 2(S77834), IL 6 (BC015511), TNF-beta (X02911), FAS (KM114217), BAX 1 (NM_001291428), Caspase-3 transcript variant 1 (NM_004346), Caspase-8 (AB038985), C5a (M59863), C3 (K02765), MHC class II DN alpha (M26039), TLR4 (U88880), TLR6 (BC111755), UVRAG (AB012958), ATG3 (NM_022488), Beclin 1 (NM_003766). Without limiting the type of apoptotic gene, in one embodiment, the apoptotic gene comprises p53 gene. While not intending to limit the sequence of the siRNA, in one embodiment, the siRNA comprises any one or more of the exemplary siRNA sequences of FIG. 7A-D. In one embodiment, the siRNA comprises one or more p53 gene siRNA, exemplified by p53 siRNA sequences of FIG. 7A-D, such as GCAT-GAACCGAGGCCCAT (SEQ ID NO: 1). In one embodiment, the p53 gene siRNA comprises an RNA sequence that specifically binds with mRNA encoded by p53 gene sequence 5'-GCATGAACCGAGGCCCAT-3' (SEQ ID NO: 1) or by the complement thereof. In a particular embodiment, the p53 gene siRNA comprises one or both of p53 sense siRNA 5'-r(GCAUGAACCGAGGCCCAU)dTdT-3' (SEQ ID NO: 2) and p53 antisense 5'-r(AUGGGCCUCG-GLIUCAUGC-dTdT-3' (SEQ ID NO: 3). Without limiting the type of perfusion, perfusion is exemplified by one or more of normothermic perfusion and/or sub-normothermic perfusion and/or hypothermic perfusion. While limiting the type of target tissue used in the invention's methods, the tissue is exemplified by liver, heart, lung, heart/lung, kidney, pancreas, intestine, stomach, testis, hand, cornea, skin, islets of Langerhans, bone marrow/adult stem cell, blood, blood vessel, heart valve, and bone. In one embodiment, the tissue is liver tissue. In one embodiment, the apoptotic gene comprises a FAS receptor gene. In a particular embodiment, the RNAi sequence comprises an siRNA sequence that specifically binds with mRNA encoded by one or more of FAS receptor gene sequences 5'-GCAGGCCAAGTTGCT-GAAT-3' (SEQ ID NO: 4), 5'-GGCCAAGTTGCTGAAT-CAA-3' (SEQ ID NO: 5), 5'-GCCAAGTTGCTGAAT-CAAT-3' (SEQ ID NO: 6), 5'-TCGTGAGCTCGTCICIGAT-3' (SEW ID NO: 7), and 5'-CCCGCGCGCAGGCCAAGTT-3' (SEQ ID NO: 8), or with the complement of any thereof (illustrated in Example 3). In a further embodiment, the FAS receptor gene siRNA comprises one or both of FAS receptor gene sense siRNA and anti sense siRNA (Example 3). In a particular embodiment, the FAS receptor gene sense siRNA comprises one or more of 5'-GUGCAAGUGCAAACCA-GACdTdT-3', 5' (SEQ ID NO: 9)-AGCCGAAUGU-CGCAGAACCdTdT-3' (SEQ ID NO: 10), 5'-GGAUUAUAUCAAGGAGGCCdTdT-3' (SEQ ID NO: 11), 5'-AUCGCCUAUGGLIUGLTUGACdTdT-3' (SEQ ID NO: 12), 5'-AUACAUCCCGAGAAUUGCUdTdT-3' (SEQ ID NO: 13), and 5'-AAGCCGAAUGUCGCAGAACdTdT-3' (SEQ ID NO: 14). In a further embodiment, the FAS receptor gene sense siRNA comprises 5'-GUGCAAGLJGCAAACCAGACdTdT-3' (SEQ ID NO:9). In another embodiment, the FAS receptor gene antisense siRNA comprises one or more of 5'-GUCUG-GUUUGCACUUGCACdTdT-3' (SEQ ID NO: 15), 5'-GUIICUGCGACALUCGGCUdTdT-3' (SEQ ID NO: 21), 5'-GGCCUCCUUGAUAUAAUCCdTdT-3' (SEQ ID NO: 16), 5'-GUCAACAACCAUAGGCGAUdTdT-3' (SEQ ID NO: 17), 5'-AGCAAUUCUCGGGAUGUAUdTdT-3 (SEQ ID NO: 18), and 5'-GUUCUGCGACAUUCGGC-UUdTdT-3 (SEQ ID NO: 19) . In another embodiment, the FAS receptor gene antisense siRNA comprises 5'-GUCUG-GUUUGCACUUGCACdTdTCy3-3' (SEQ ID NO: 20). While not intending to limit the invention to any particular temperature, the contacting step comprises a normothermic temperature, exemplified in Examples 1-3 using a temperature of 37° C. In a further embodiment, the contacting step comprises a hypothermic temperature, exemplified in Examples 2 and 3 using a temperature of 4° C. In a further embodiment, the contacting step comprises a sub-normothermic temperature.

Figure 3:
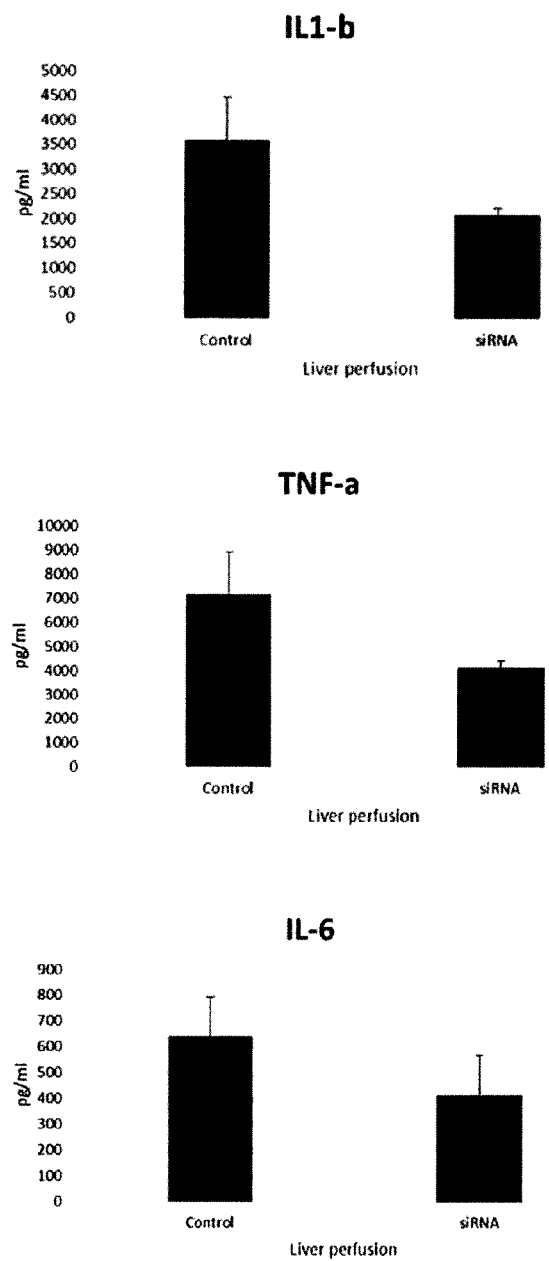

FIG. 3. Inflammatory cytokines assessed by ELISA analysis of perfused livers treated with p53 siRNA versus untreated controls.

Figure 4:
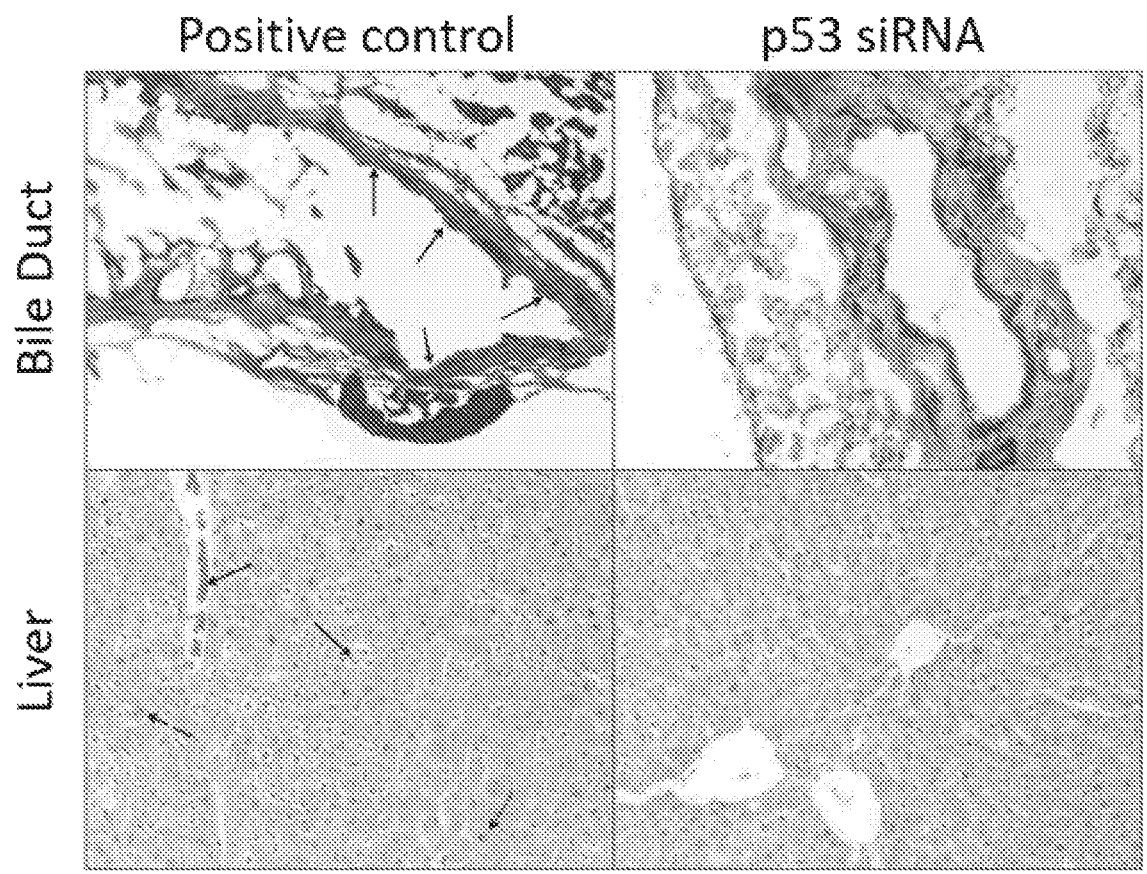

FIG. 4. Histological analysis of bile ducts (upper panel) and liver parenchyma (lower panel) treated with p53 siRNA (right panel) or non treated positive control (H&E staining).

Figure 5:
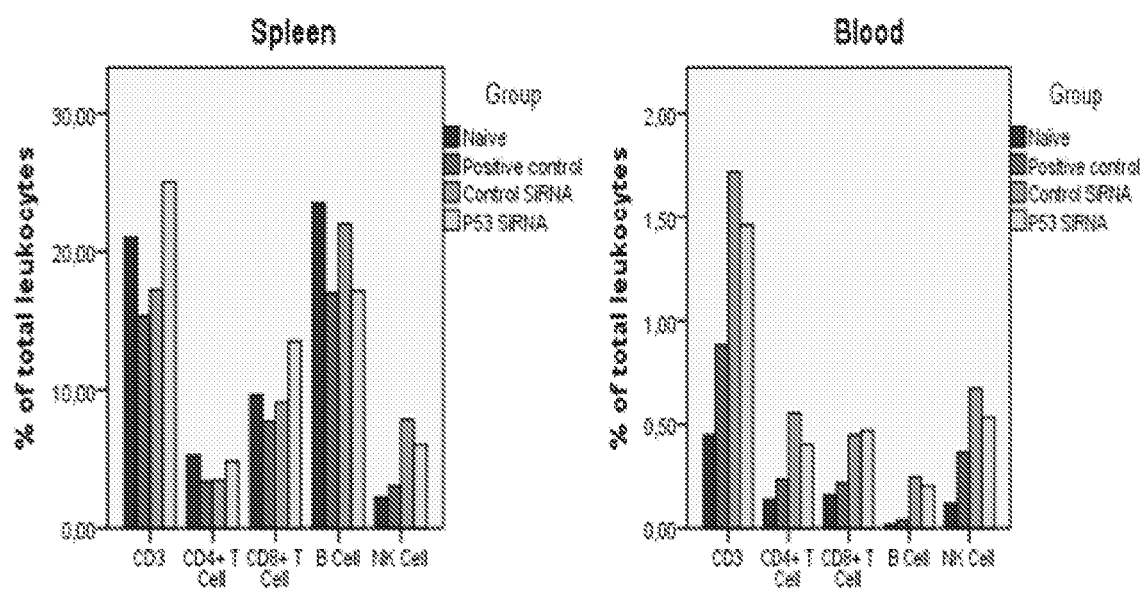

FIG. 5. Flow cytometry analysis of peripheral blood and splenocytes treated with p53 siRNA and the corresponding control groups. Flow cytometry analysis showed that p53 siRNA has no effect on the relative distribution of immune cell populations such as total lymphocytes, CD4, CD8, NK cells, neutrophils, monocytes and B cells, in the blood nor the spleen (FIG. 3). This gives us evidence of a direct effect on the liver itself.

Figure 6:
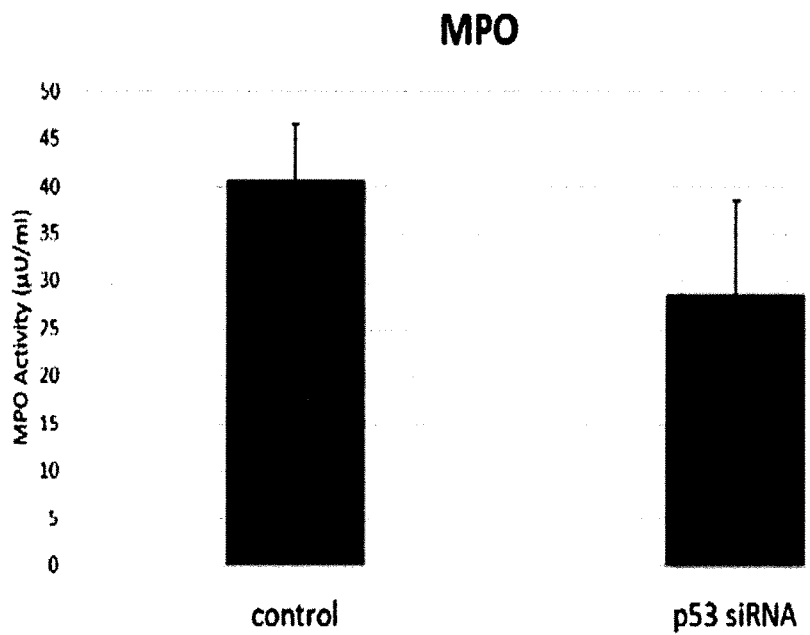

FIG. 6. Neutrophil infiltration assessed by myeloperoxidase analyses of clamped livers treated with p53 siRNA versus untreated controls.

FIG. 7A-D. Exemplary siRNA sequences that may be used in the invention's methods.

Figure 8:
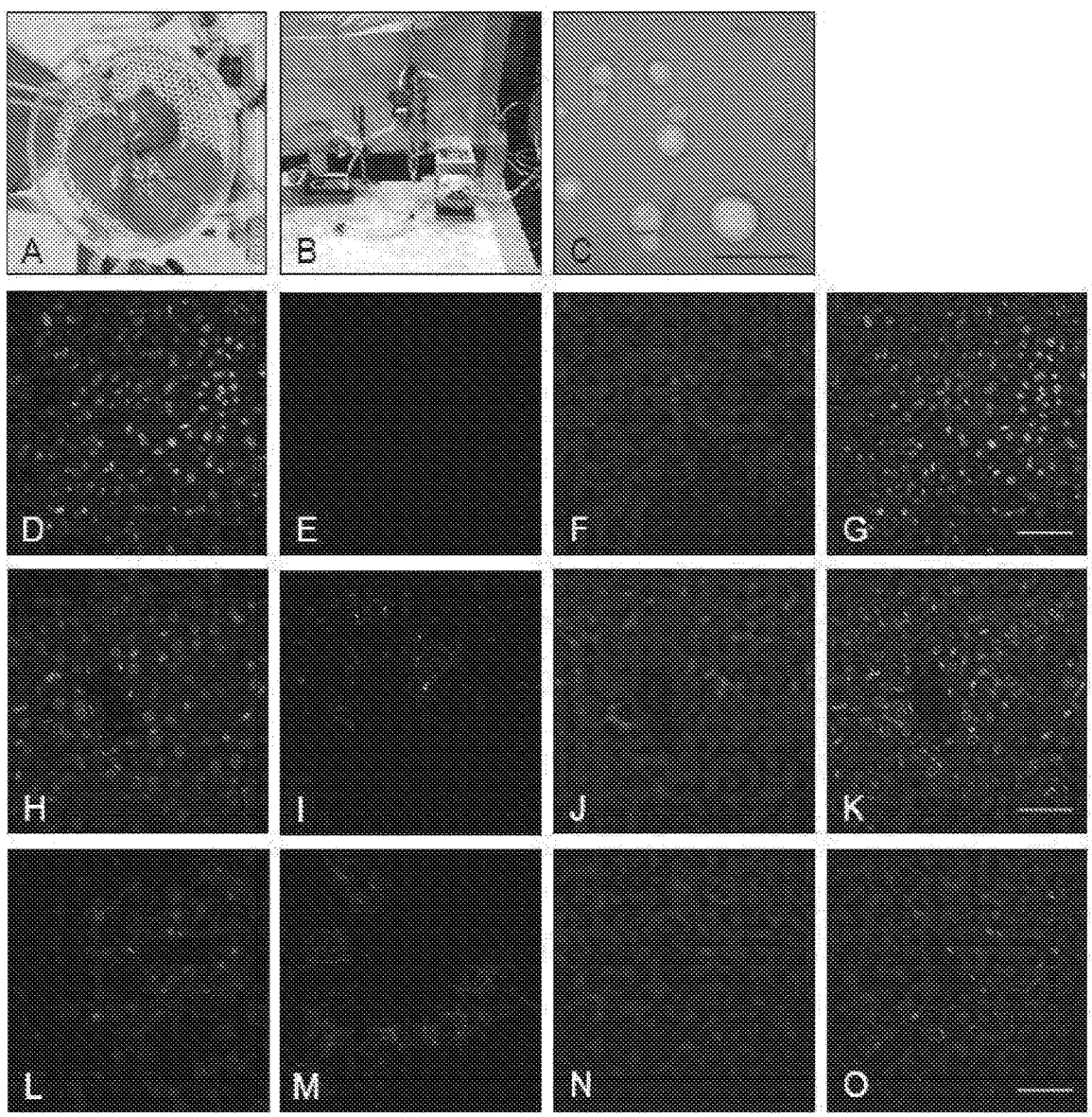

FIG. 8: FAS siRNA uptake in rat hepatocytes during hypothermic (4° C.) and normothermic (37° C.) ex vivo machine perfusion. Scale represents 20 μm. Adult male rat livers were harvested and the portal vein cannulated (arrow) with a modified angiocatheter (A). Livers were perfused via the cannula on a closed-loop circuit with a roller pump, warmed or cooled by a circulating water bath. Portal vein pressure was maintained at 10 mmHg. (B). Empty lipid nanoparticles were imaged with electron microscopy; scale represents 200 nm (C). Perfusion solution was comprised of Williams medium E supplemented with 10 U insulin. Control livers were perfused with medium plus Invivofectamine (ThermoFisher) transfection lipid nanoparticles (D-G) for four hours.

Figure 9:
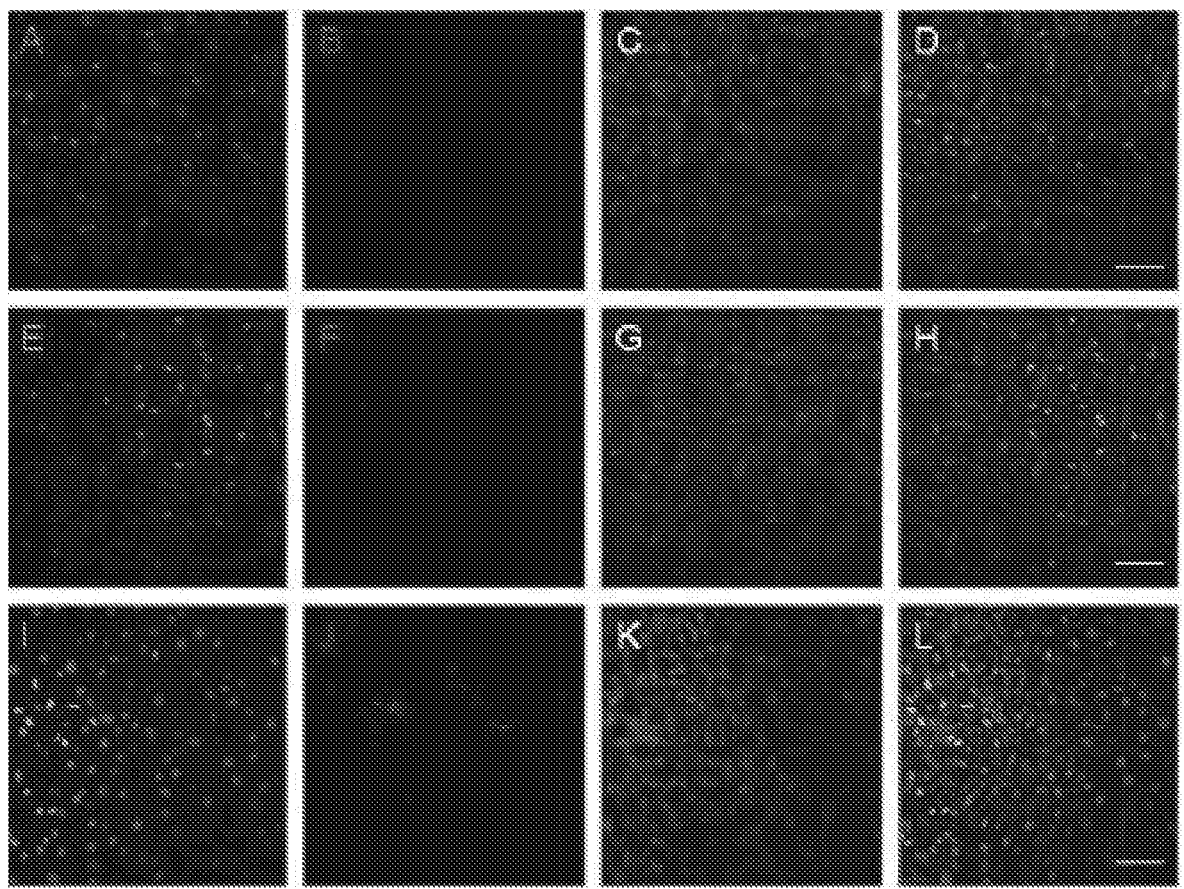

FIG. 9: Alexa Fluor conjugated p53 siRNA (1 mg/kg of liver) is uptaken by rat hepatocytes during normothermic machine perfusion with Williams E media. Scale represents 20 μm. A-D: Untreated liver (no lipofectamine or siRNA) before machine perfusion. Nuclei visualized in blue with DAPI (A), siRNA in green (B), cell membranes in red with wheat germ agglutinin conjugated to Alexa Fluor 647 (C), with merged image in (D).

DEFINITIONS

To facilitate understanding of the invention, a number of terms are defined below.

"Ischemia," refers to a deficient supply of blood, and thus oxygen, to a tissue. In some embodiments, ischemia is due to obstruction of the inflow of arterial blood.

"Ischemic injury," "ischemic event," "injury resulting from ischemia," "injury caused by ischemic," and interchangeably refer to any reduction in the viability and/or function of a tissue caused by ischemia. Ischemic injury is exemplified by apoptosis, inflammation, and neutrophil infiltration, and may result from, for example, brain death, organ harvesting, ischemia reperfusion (referred to as "I/R." or "IR"), "Ischemia reperfusion injury," "ischemia/reperfusion injury," and "IRI" interchangeably refer to a type of ischemic event that is characterized biochemically by a depletion of oxygen during an ischemic event involving interrupted blood flow followed by reoxygenation and the concomitant generation of reactive species during reperfusion. IRI is exemplified by, but not limited to, tissue damage (e.g., tissue inflammation, release by the stressed endothelial cells of inflammatory mediators such as platelet activating factor (PAF), tumor necrosis factors (such as TNFα) and a panel of interleukins (ILs) (such as IL-1b, IL-6), increased expression of cellular adhesion molecules for leukocytes on the cell surface, reduction of nitric oxide (NO) production, shrinkage of the vascular lumen, decreased oxygen supply to the organ's parenchyma, increased vascular permeability (vascular leakiness), and neutrophil accumulation. Also, invading immune cells release supplementary reactive-oxygen species (ROS), proteases and inflammatory mediators, also increasing the IRI. IRI affects all organs and is manifested in the context of transplantation by delayed graft function (DGF), decreased duration of graft survival (DGS), increased risk of acute and/or chronic rejection.

"Perfusion" refers to circulation of a preservation solution through the blood vessels of a tissue. Such perfusion helps to sustain or replenish residual, intracellular energy stores while also reducing the rate at which they are consumed. Perfusion includes "machine perfusion" and "machine preservation," which interchangeably refer to pump-driven perfusion. Perfusion may be "normothermic" i.e., at the physiological temperature of the donor tissue, i.e. 37° C. for human donors, 38° C. for mouse and rat donors, etc. Perfusion may be "sub-normothermic" i.e., at a temperature from 20° C. to any temperature less than the physiological temperature of the donor tissue, e.g., from 20° C. to less than 37° C. for human donors, from 20° C. to less than 38° C. for mouse and rat donors, etc. Perfusion may be "hypothermic" i.e., at a temperature below 20° C., such as from 4° C. to less than 20° C.

"Apoptosis" is a process of programmed cell death that is characterized by changes in cell morphology and death. These changes include blebbing, cell shrinkage, nuclear fragmentation, chromatin condensation, chromosomal DNA fragmentation, and mRNA decay.

"Inflammation" refers to a cascade of biochemical events involving the vascular system and the immune system. Inflammation is associated with changes in the levels of molecules such as interleukins, histamines, serotonins, eicosanoids, nitric oxide, complement, lysozymes, and antibodies, as well as changes in the complement system, and the kinin system. Inflammation is also associated with leukocyte infiltration, particularly neutrophil infiltration.

"Neutrophil infiltration" refers to the movement of neutrophils from the blood through the blood vessels to tissues.

"Autophagy" is an intracellular degradation system that delivers cytoplasmic constituents to the lysosome. It is a natural, regulated, destructive mechanism of the cell that disassembles unnecessary or dysfunctional components.

"RNA interference" and "RNAi" refer to a biological process in which double-stranded RNA induces the activation of endogenous cellular pathways of RNA degradation resulting in selective and potent silencing of genes post-transcriptionally that have homology to the double strand. RNA interference sequences are exemplified by "microRNA" (miRNA) sequences and "small interfering RNA" (siRNA) sequences.

"Small interfering RNA" "siRNA" and "short interfering RNA" refers to a synthetic, man-made, double-stranded RNA molecule that specifically binds to a complementary sequence in mRNA, thus interfering with the expression of specific genes with complementary nucleotide sequences by degrading the mRNA after transcription and consequently preventing translation. Exemplary siRNA sequences that are useful in the invention's methods are shown in FIG. 7A-D.

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general, the siRNAs must retain specificity for their target, i.e., must not directly bind to, or directly significantly affect expression levels of, transcripts other than the intended target. Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference. In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The terms "specifically binds," "specific binding," and grammatical equivalents, when made in reference to the binding of siRNA to a polynucleotide sequence (such as mRNA), refer to binding of the siRNA with a complementary sequence on the mRNA.

"Contacting" a tissue with siRNA includes administering and/or delivering the siRNA to the tissue, such as by including the siRNA in a fluid (such as saline, plasma, heparinized whole blood, etc.). For example, during perfusion of the tissue, siRNA may be included in the perfusate at a concentration from 0.5 to 2 µg/ml perfusate, pH from 7.3 to 7,4, for a period of from 1 to 48 hours, more preferably from 2 to 24 hours. In one embodiment, perfusion is for 4 hours. The perfusate is exemplified by oxygenated fluids such as UW MPS solution, Williams E solution, heparinized whole blood, etc., at an exemplary perfusion pressure of from zero to 5 mmHg.

The term "gene that mediates ischemic injury" in a tissue refers to a gene that directly or indirectly causes ischemic injury e.g., by expressing a protein that causes ischemic injury. This term also includes genes are directly or indirectly associated with ischemic injury, even if they do not directly cause such injury.

"Mammal" includes a human, non-human primate, murine (e.g., mouse, rat, guinea pig, hamster), ovine, bovine, ruminant, lagomorph, porcine, caprine, equine, canine, feline, aye, etc. In one preferred embodiment, the mammal is murine. In another preferred embodiment, the mammal is human.

"Tissue" refers to an organized ensemble of cells and their extracellular matrix from the same origin that together carry out a specific function. Tissues are exemplified by those used in tissue transplantation from a transplant donor such as tissue from the hand, cornea, skin, including face replant (autograft) and face transplant, islets of Langerhans (pancreas islet cells), bone marrow/adult stem cell, blood transfusion/blood parts transfusion, blood vessels, heart valve (deceased-donor, living-donor and xenograft (porcine/bovine)), and bone. The term "tissue" includes an "organ," which is formed by the functional grouping together of multiple tissues. The term "tissue" also includes portions of tissues, and portions of organs (e.g., lobe of a lung or of a liver). Organs are exemplified by those used in organ transplantation from a transplant donor, such as liver, heart, lung, heart/lung, kidney, pancreas, intestine, stomach, and testis.

"Therapeutic amount," and "therapeutically effective amount" are used interchangeably herein to refer to an amount that is sufficient to achieve a desired result, such as treating ischemic and/or reducing the level and/or rate of apoptosis, and/or reducing the level of one or more Interleukin (e.g., IL-1b, IL-6, and TNF-α) in a tissue (see FIG. 3), and/or reducing the level and/or rate of neutrophil infiltration into a tissue (see FIG. 6).

The term "ex vivo" refers to an environment outside an organism.

"Transplant donor" is a mammalian subject from whom a transplant tissue is obtained prior to transplantation of the tissue to a transplant recipient. The transplant donor may be living or deceased.

"Transplant recipient" is a mammalian subject into whom a transplant tissue is placed after excision or removal of the tissue from the transplant donor, "Treating" ischemia means reducing the level and/or rate and/or severity and/or risk of ischemia, This may include "treating ischemic injury," which means reducing the level and/or rate and/or severity and/or risk of ischemic injury.

The terms "reduce," "inhibit," "diminish," "suppress," "decrease," and grammatical equivalents (including "lower," "smaller," etc.) when in reference to the level and/or rate of change in the amount and/or concentration of any molecule cell, and/or phenomenon (e.g., amino acid sequence such as IL-1b, IL-6, and TNF-α, nucleic acid sequence, antibody, symptom, ischemia, ischemic injury, gene expression, apoptosis, neutrophil infiltration, inflammation, specificity of binding of two molecules, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may he different, such as when comparing the effect of the invention's compositions and/or methods on one sample (subject), for example a patient participating in a clinical trial and another individual in a hospital.

The terms "increase," "elevate," "raise," and grammatical equivalents (including "higher," "greater," etc.) when in reference to the level and/or rate of change in the amount and/or concentration of any molecule cell, and/or phenomenon (e.g., amino acid sequence such as IL-1b, IL-6, and TNF-α, nucleic acid sequence, antibody, symptom, ischemia, ischemic injury, gene expression, apoptosis, neutrophil infiltration, inflammation, specificity of binding of two molecules, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

"P53", "Tumor Protein P53", "Phosphoprotein P53", "Transformation-Related Protein 53", "Cellular Tumor Antigen P53", "Mutant Tumor Protein 53", "P53 Tumor Suppressor", "Tumor Suppressor P53", "Tumor Supressor P53", "Tumor Protein 53", "TRP53", "BCC7" and "LFS1" interchangeably refer to a protein sequence exemplified by GenCard Identifier (GGID): GC17M007661, GC17P008026, GC17M008311, GC 17M007514, GC17M007772, GC17M007512, GC17M007565, and GC17M; HGNC: 11998; Entrez Gene: 7157; Ensembl: ENSG00000141510; OMIM: 191170; and UniProtKB: P04637007465.

"Rejection" of a target tissue by a mammalian subject that is transplanted with a tissue includes undesirable clinical and/or biochemical symptoms, including a reduction in the transplanted tissue's function. For example, rejection of liver transplants comprises symptoms such as jaundice, dark urine, itching, abdominal swelling or tenderness, fever, discomfort or feeling ill, body aches, nausea, cough, and shortness of breath.

"Immunological tolerance" by a recipient mammalian subject to a transplanted tissue refers to the recipient's immune system preventing attack and destruction of the transplanted tissue that would otherwise lead to graft rejection. Immunological tolerance is desirable since the recipient transplant subject can be weaned from immune suppressive drugs.

BRIEF DESCRIPTION OF THE INVENTION

The invention provides methods for treating ischemia in a target tissue, comprising contacting the tissue, during ex vivo perfusion of the tissue, with a therapeutically effective amount of RNAi (such as siRNA) that specifically binds to at least a portion of a gene that mediates ischemic injury in the tissue, thereby producing a treated tissue. To date, gene silencing using siRNA has not been performed during ex vivo perfusion of tissue, such as organ gratis.

While not intending to limit the type of ischemic injury that is treated by e invention's methods, ischemic injury is exemplified by, but not limited to, apoptosis, inflammation, and neutrophil infiltration. While it is not intended to limit the type of therapeutically effective amount of siRNA, in one embodiment, the therapeutically effective amount of RNAi (such as siRNA) reduces one or more of i) the level and/or rate of apoptosis mediated by the gene in the treated tissue compared to a control tissue that is not contacted with the therapeutically effective amount of siRNA, ii) the level of one or more of IL-1b, IL-6, and TNF-α in the treated tissue compared to a control tissue that is not contacted. with the therapeutically effective amount of siRNA (exemplified in FIG. 3), and iii) the level and/or rate of neutrophil infiltration into the treated tissue compared to a control tissue that is not contacted with the therapeutically effective amount of siRNA (exemplified in FIG. 6). Exemplary siRNA sequences that are useful in the invention's methods are shown in FIG. 7A-D.

While not intending to limit the treatment of the target tissue and/or treated tissue, in one embodiment, one or both of the target tissue and the treated tissue is disconnected from a mammalian subject's circulatory system. In one exemplary embodiment, the contacting step is prior to transplanting the treated tissue to a mammalian recipient. In another exemplary embodiment, the method further comprises the step of transplanting the treated tissue into a transplant recipient. Also, the type or source of the target tissue is not intended to be limited to a particular type of tissue, and includes the exemplary liver tissue, liver organ, and portions thereof.

While not intending to limit the type of gene that mediates ischemic injury in the tissue, in one embodiment, the gene is exemplified by one or more apoptotic gene (e.g., p53, FAS, BAX, caspase-3, caspase 8), and/or inflammatory gene (e.g., NFK-B TN-γ, TNF-α, IL-1, IL-2, IL-6, TNF-β), and/or complement gene (e.g., c5a, C3), and/or major complex antigen gene (e.g., MHC class II), and/or Toll like receptor gene. In one embodiment, the apoptotic gene comprises p53 gene, and the p53 gene siRNA comprises GCAT-GAACCGAGGCCCAT (SEQ ID NO: 1) (Example 1). The perfusion of the issue is not limited to a particular type of perfusion, and includes normothermic perfusion, and/or sub-normothermic perfusion, and/or hypothermic perfusion.

The invention's methods provide the advantage of improving transplant outcomes and improving transplant logistics by extending the period for organ allocation and transport. In addition, the invention's methods allow "reconditioning" of grafts that are initially deemed not transplantable, thus increasing the pool of organs available and consequently decreasing the waiting time and mortality on the liver transplant waitlist.

The invention's exemplary ex vivo graft therapy also has the advantage of reducing side effects related to systemic therapy. Because a graft is metabolically functional during normothermic perfusion, there will potentially be a more effective treatment response in a shorter period of time in comparison to cold perfusion (Medzhitov R 1997, Akimoto 2014, Volpe 2010, Magin 1984, Basak 2013, Ballard 1964 and 1974). In addition, treating the organ ex vivo instead of treating the recipient has the advantages of requiring smaller doses, reducing treatment costs, and avoiding systemic side-effects associated to recipient treatment. Treating the organ ex vivo also bypass logistical limitations of treating a multi-organ cadaver donor (not all transplant centers may agree with systemic donor treatment).

Another of the advantages of the invention's exemplary RNAi (such as siRNA) therapy is its specificity and reduced side effects. RNAi (such as siRNA) provide a very selective effect on the targeted gene that will reduce ischemia reperfusion injury without interfering with long-term graft function. In addition to its selectivity, the genetic modulation with RNAI (such as siRNA) is transitory, lasting only several days, which is the critical time when ischemia reperfusion injury takes place.

MORE DETAILED DESCRIPTION OF THE INVENTION

1. Ex Vivo Graft Treatment

Cirrhosis is the tenth leading cause of death in the United States, killing about 30,000 people each year with an estimated annual cost of $10.6 billion (Neff GW 2011). Liver transplantation provides lifesaving treatment for patients with end-stage liver disease. However, the current disparity between supply and demand of liver grafts has exponentially increased the waiting time and mortality on the waitlist. The average waiting time in many regions can be longer than one year and the mortality on the waitlist is between 10 and 20% (UNOS). Despite the increasing organ shortage, 20% of liver grafts are still discarded because of poor organ quality, especially in regards to severe ischemic insult. Ischemic liver grafts from donors after cardiac death (DCD, also known as non-heart-beating donors) are associated with worse outcomes (including bile duct complications) account for the high discard rate. There are several experiments showing that machine preservation (pumping perfusate continuously through the organ) is superior to the standard static cold storage (graft stored in a container with ice). Recently, machine preservation of kidney grafts became the gold standard. Few clinical trials using machine preservation for liver grafts have shown promising results. However, they did not investigate biliary injury in detail and did not test ischemic grafts.

Graft quality and immunogenicity determine, at least in part, the success of organ transplantation. The graft is not only the target, but may also direct the host immune response. Indeed, innate and adaptive immune responses act in concert and can be influenced by donor treatment.

Many studies have shown a strong association between initial graft injury and poor long-term graft outcome. Events initiated by unspecific immune-activating processes including brain death and ischemia/reperfusion injury occurring prior to transplantation reduce graft functionality and amplify the host immune response. These events may be particularly relevant for less than optimal grafts with reduced resistance to unspecific injuries. Several approaches to ameliorate immune activation of the graft by treating the donor or the graft have been studied. While various substances have been shown to have protective effects in experimental transplantation, only a few drugs have been tested clinically and have demonstrated beneficial effects.

After brain death, a series of neural, hormonal, and molecular changes occur, resulting in. cellular stress and inflammatory response (Pratschke J 2004, Van der Woude FK 2002). These events lead to reduced cell defense mechanisms and increased graft immunogenicity inducing a host alloimmune response even in the absence of non-self antigens. It is hypothesized that the initial injury initiates allograft rejection by activating complement and coagulation pathways, recruiting inflammatory cells, promoting trafficking of dendritic cells (DCs) into the allograft, inducing the expression of major histocompatibility complex (MHC) molecules and costimulatory signals, as well as regulating T-cell differentiation (Schuurs). The initial graft injury associated with brain death, the harvesting procedure, and consequences of I/R limit the function of 'marginal grafts' even more (Tullius 2004, Johnson 2004, Medzhitov 1997). Many studies have shown a strong association between organ quality, nonspecific damages prior to transplantation and poor long-term graft outcome (Geddes 2002, Ojo 1997, Leggat 1997, Tropmann 1995, Cosio 1997). Interactions between the innate and adaptive immune response may be implicated in the association of ischemia reperfusion injury with acute and chronic rejection (Koga S1999). It has been shown that the innate immune response has a major influence on the adaptive immunity by enhancing T-cell priming (Takeda K 2003), The innate immune system produces cytokines and chemokines that are critical for the trafficking of activated T cells.

All cells in the graft but especially DCs are able to initiate an immune response. Parenchymal cells are not just targets of the alloresponse, but also play an active role in the rejection process. Stimulated by inflammatory conditions initiated after brain death, the harvesting procedure and amplified by UR injury, parenchymal cells can overexpress MHC antigens, produce inflammatory cytokines and adhesion molecules, and finally undergo apoptosis. Under those circumstances, these cells can also express MHC class II antigens (Van der Woude 2002, Wood 2003).

Activation of DCs in this scenario is of particular relevance for the increase in graft immunogenicity (Hart DN 1981). Solid and cellular grafts contain DCs in an immature stage (Ibrahim 1995). There is an increasing body of evidence showing that DCs are activated by 'danger signals', substances produced by distressed or injured cells (DNA, heat-shock proteins, inflammatory cytokines, breakdown products of cellular membrane, etc.) (Matzinger 2002). This initial injury provides the maturation signals that DCs need to migrate and induce T-cell activation Game). When DCs mature in the presence of inflammatory signals, they increase the expression of class I and II MHC antigens and costimulatory molecules, thus increasing the production of cytokines and amplifying the immune response. In addition, when donor DCs die in the recipient's lymph nodes, they can cross-prime antigens through the indirect pathway of allorecognition (Hackstein 2004, Takeda 2003, Karmann 1995, Raftery 1989, Rosendale 2002).

Minimizing initial cellular stress and damage associated with an inflammatory immune response may impact the overall need for post-transplant immunosuppression while increasing the availability of organs for transplantation (Wheeldon 1995, van der Woude 2002, Valero 2002, Lee 1996). The time between the diagnosis of brain death and organ harvesting, as well as the storage period, could be used to prevent or minimize graft immune activation.

Donor therapy may be particularly relevant for the transplantation of extended criteria grafts, which are less apt to cope with cellular stresses. Various strategies have been used for donor/graft treatment. Those include pharmacotherapy (immunosuppressive, anti-inflammatory and chemotherapy drugs, cytokines, vasoprotective agents, monoclonal antibodies, and antioxidants), irradiation (gamma or ultraviolet irradiation of the graft), cell transfer experiments (bone marrow cells, blood, splenocytes, DC, and lymphocytes), temporary controlled-warm ischemia (ischemic preconditioning), and gene therapies (liposomes and virus vectors).

These approaches were accomplished either by treating the graft itself during perfusion or cold storage or by treating the donor prior to graft procurement. Treating the donor has the advantage of preserved cellular metabolic pathways, while most pharmacological agents are inactive or insoluble in hypothermic preservation solutions. In addition, poor permeability of membranes and inhibited active transport mechanisms in hypothermic conditions may compromise drug access (Biguzas 1990, Brasile 2002). Similarly, genetic modification of organs is limited as viral vectors have a very limited transfection rate under these conditions (Southard J H 1995).

Ex vivo machine preservation reduces the accumulation of toxic substrates and free radical formation on reperfusion, thus minimizing the consequences of UR injury. Continuous perfusion permits, in theory, also the use of normothermic solution, which is more appropriate to promote active graft modulation.

When cell metabolism is maintained, both pharmacological agents and viral vectors are more efficient in promoting protection. Gene therapy, although very selective, is frequently limited by low transfection rates, transient gene expression, and a potential immune activation because of viral-vectors (Southard J H 1995, Pratschke J 2000).

2. Gene Silencing with RNAi (Such as siRNA) During Liver Machine Preservation to Alleviate Ischemia Reperfusion Injury of Ischemic Liver Grafts RNA interference (RNAi.) is a process through which double-stranded RNA induces the activation of endogenous cellular pathways of RNA degradation resulting in selective and potent silencing of genes post-transcriptionally that have homology to the double strand. Much of the excitement surrounding small interfering RNA (siRNA)-mediated therapeutics arises from the fact that this approach overcomes many of the shortcomings previously experienced with alternative approaches to selective blocking like antibodies, antisense oligonucleotides, and pharmacological inhibitors. In addition, it is very selective and can be applied ex vivo. Induction of RNAi through administration of siRNA has been successfully applied to the treatment of hepatitis, viral infections, and cancer. One of the main injuries associated with organ transplant is the initial inflammation and apoptosis that occurs in the first few days after reperfusion (Wheeldon D R 1995). Prevention of inflammation and apoptosis is extremely important to reduce initial organ damage that can lead to perpetuation of injury and organ failure. We tested for the first time whether we can modulate the transcription of apoptotic genes during machine preservation of livers with siRNA and more specifically if we can decrease the rate of apoptosis on the distal bile duct, by targeting p53-mediated apoptosis.

3. p53 Gene and the Effect on Graft Apoptosis p53 is a gene that codes for a tumor suppressor protein/transcription factor. It is activated by various stresses such as hypoxia, free radicals, and DNA damage. When activated, it induces the transcription of death proteins such as bax, Peg3, Apaf1, p53AIP1 and Fas leading to apoptosis. Synthetic small interference RNA (siRNA) targeting p53 has been tested in reducing renal ischemic injury (Ying Y 2014).

4. Discussion of Example 1

The experiments in Example 1 demonstrate that transcription of apoptotic genes can be modulated during machine preservation of livers using siRNA, and more specifically demonstrated that the invention's methods decreased the rate of apoptosis on the distal bile duct of the perfused tissue.

Data herein in Example 1 also demonstrate that gene silencing successfully modulates the transcription of genes (such as the apoptotic gene p53) during ex vivo machine preservation of tissue (such as liver).

Data herein in Example 1 show that p53 siRNA (GCAT-GAACCGAGGCCCAT) (SEQ ID NO:1) reduced the transcription of the target p53 gene, and reduced the expression of inflammatory cytokine (IL-1, IL-6, TNFα) in both serum and liver tissue. This treatment did not result in significant changes in the cell populations in blood. This siRNA was taken up by the liver during ex vivo normothermic machine preservation. Thus, p53 siRNA ex vivo delivery during machine preservation decreases apoptosis and alleviates ischemia reperfusion injury of liver grafts.

EXPERIMENTAL

The following examples serve to illustrate certain preferred embodiments and aspects of the present invention and are not to be construed as limiting the scope thereof.

EXAMPLE 1

Ischemic (DCD) Rat Livers can be Reconditioned with Machine Perfusion

The overall goal of the following experiments was to improve the quality of suboptimal (ischemic) liver grafts. In particular, the following experiments were conducted to investigate the effect of treatment with p53 siRNA during ex vivo machine preservation on alleviating ischemia reperfusion injury in a rat liver reperfusion and liver transplantation model. To our knowledge, gene silencing has never been tested during machine preservation of grafts.

Rats were injected with cy3-labeled p53 siRNA using a nanoparticle invivofectamine (liposome) as a carrier one day prior inducing liver damage using the hepatotoxic agent CCL4. After 3 days the rats were euthanized and samples were collected for analysis by flow cytometry, confocal microscopy and histological scoring of the liver and bile ducts.

Ischemia reperfusion injury was mimicked by a liver clamping model. The effect of p53 on alleviating the liver damage was assessed by measuring inflammatory cytokines (IL-1b, TNF-α and IL-6 measured by ELISA), and neutrophil infiltration (measured by MPO activity). Finally, livers were ex vivo perfused with p53 siRNA during machine perfusion. Liver function was assessed by measuring inflammatory cytokines IL-1b, IL-6 and TNF-α.

Figure 1:
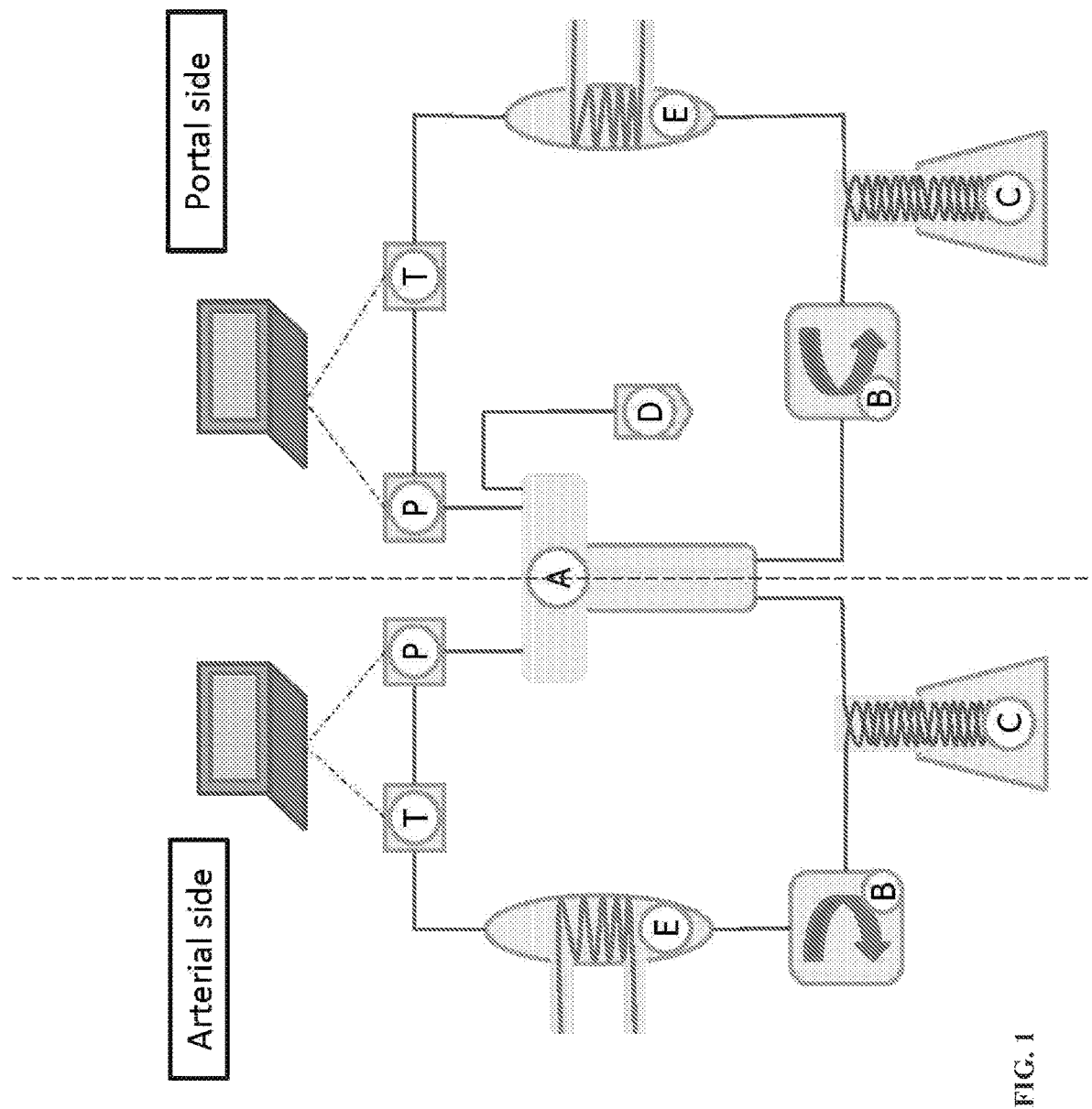
FIG. 1. Normothermic Extracorporeal Liver Machine Perfusion system.
Figure 1:
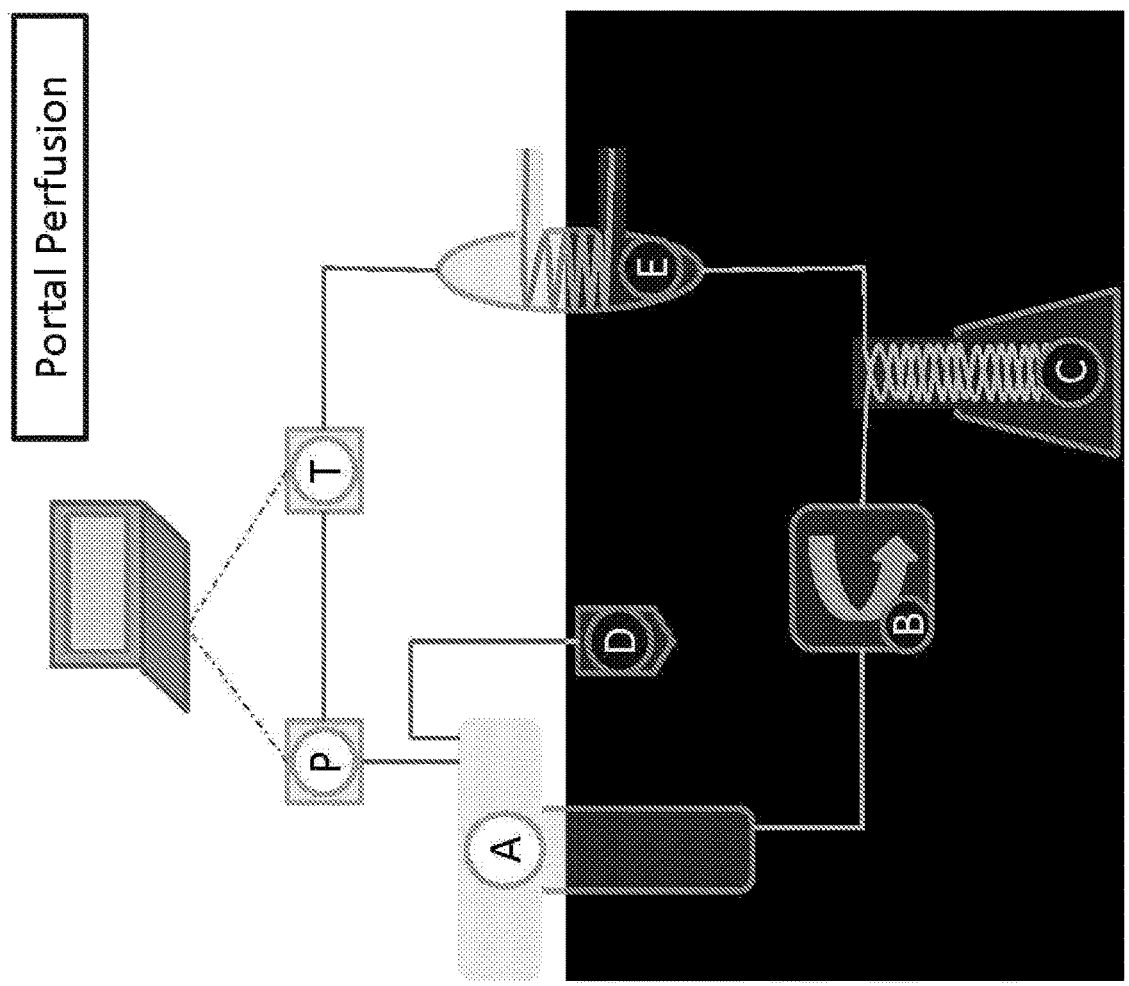
Figure 2:
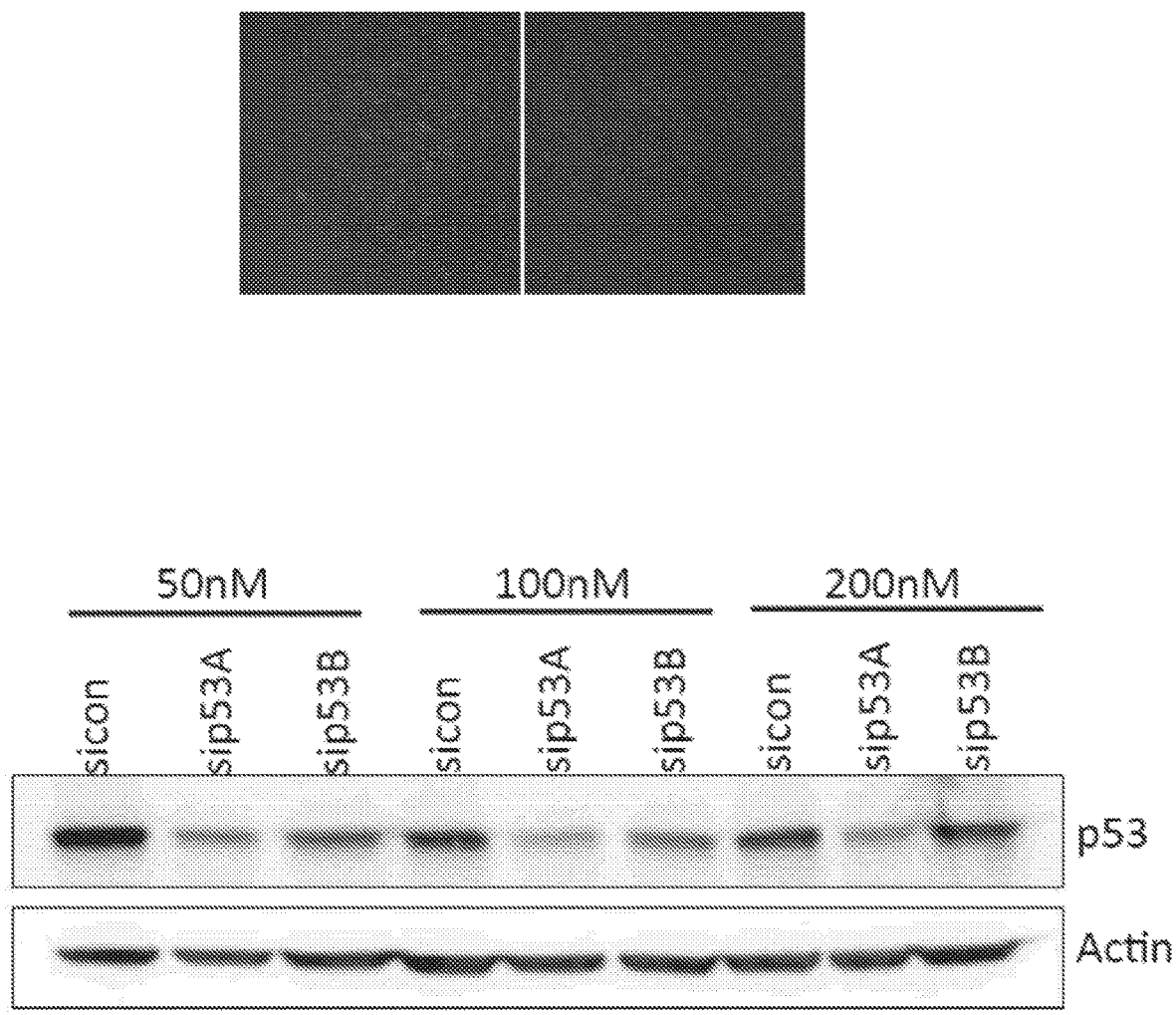
FIG. 2. Distribution of Cy3-labeled p53 siRNA (red) in the rat liver 24 hr after tail vein injection. Tissues were fixed after 24 h, processed and imaged at 10× on a Leica tiling fluorescent microscope; nuclei stained with DARI (blue). The right panel shows genetic expression silencing of p53 gene by western blot in hepatocytes culture after treatment with p53 siRNAs (si-p53A and si-p53B) at different concentrations.

A Normothermic Extracorporeal Liver Machine Perfusion (NELMP) system was used, that operates at a near physiological flow rate (FIG. 1). As a model of Donors after Cardiac Death (DCD), rat livers were harvested and held at 37° C. for 30 minutes to induce warm ischemic injury. Subsequently, the ischemic livers were perfused up to 4 hours in the perfusion system containing Cy3-labeled p53 siRNA associated to invivofectamine (liposome) added to the perfusate. Uptake of Cy3-labeled p53 siRNA in the rat liver was observed after 4 hrs. of perfusion (FIG. 1-6)

From the above, the data shows that that siRNA treatment during machine perfusion reduces the expression of p53 soon after transplantation and reduces ischemic reperfusion injury.

EXAMPLE 2

Reconditioning Ischemic (DCD) Rat Livers with Machine Perfusion

We used 21-bp siRNA together with lipid-based nanoparticles in the rat model to silence the apoptotic gene p53 at both at hypothermic (4° C.) and normothermic (37° C.) temperatures. The data show that siRNAs can be successfully delivered to rat liver grafts during machine perfusion directly from the perfusate solution, both at hypothermic (4° C.) and normothermic (37° C.) temperatures. FIG. 9 shows that Alexa Fluor conjugated p53 siRNA (1 mg/kg of liver) is uptaken by rat hepatocytes during normothermic machine perfusion with Williams E media.

EXAMPLE 3

Silencing FAS During the Ischemic Period Before Transplantation

The FAS receptor expressed in liver signals hepatocytes to apoptosis after binding its respective ligand. The following experiments were designed to determine the effect of FAS siRNA during the ischemic period before transplantation, using exemplary FAS receptor gene sequence sense siRNA 5'-GUGCAAGUGCAAACCAGACdTdT-3' (SEQ ID NO: 9) and antisense siRNA 5'-CUCUGGUUUGCAC-UUGCACdTdTCy3-3'(SEQ ID NO: 20). Healthy male Wistar Furth rats (~300 g) were housed in standard conditions per institutional regulations with free access to fresh water and plain rodent chow. An n=5 was used for each temperature of perfusion and controls. Anesthesia was induced via inhalation of 5% isoflurane and analgesia was maintained via IP injection with ketamine (60 mg/kg) +xylazine (8 mg/kg). A single dose of 100 u heparin was delivered via tail vein injection. Animals were exsanguinated via angiocatheterization of the aortic bifurcation marking the beginning of warm ischemic time. Both the splenic vein and inferior mesenteric vein were identified, ligated with 8-0 silk ties, and divided. A venotomy was performed on the anterior portal vein, which was cannulated via modified 18 g angiocath secured with a 4-0 silk tie. The infrahepatic vena cava was divided and the liver was flushed via PV cannula with 10 cc cold saline+100 u heparin. Hepatectomy was performed in standard fashion preserving some diaphragmatic tissue. Livers were immediately perfused on a continuous closed loop circuit by roller pump, warmed (to 37° C.) or cooled (to 4-7° C.). Portal vein perfusion pressure was maintained electronically at 10 mmHg. Warm ischemia time ended upon initiation of machine perfusion and was on average 25 minutes, A standard perfusate was made by combining 99 mL. Williams E media (ThermoFisher) with 10 U insulin. Invivofectamine lipid nanoparticles (ThermoFisher) were complexed via manufacturer protocol to FAS siRNA modified at 3' with AlexaFluor-555 (Qiagen), diluted to 1 mL in saline, then mixed with perfusate to a final concentration of 50 nM siRNA. Control livers were perfused with perfusate plus invivofectamine alone in the same volume. Liver biopsies were obtained before perfusion and after 4 hours of perfusion, fixed in formalin, and paraffinized. Sections were rehydrated in standard fashion in xylene, ethanol and water. Parenchyma was stained with wheat germ agglutinin conjugated to AlexaFluor-488 (ThermoFisher) and DAPI (VectorShield). Slides were imaged on a Nikon A1 confocal microscope and images edited with ImageJ software.

Transfection into hepatocytes was achieved by coating siRNA with lipid nanoparticles, which facilitated endocytosis across cell membranes and released siRNA into the cytoplasm (Jayaraman et al. Maximizing the Potency of siRNA Lipid Nanoparticles for Hepatic Gene Silencing in Vivo. Angew Chem Int Ed Engl 2012; 51:8529-33). SiRNA-lipid complexes were delivered in perfusion solution via portal vein cannulation and distribution was observed with fluorescent confocal microscopy. The results are shown in FIG. 8.

FIG. 8 shows that livers perfused with medium plus Invivofectamine complexed with 50 nM FAS siRNA (Qiagen) at 37° C. for 4 hours demonstrated diffuse uptake in sinusoids and surrounding central veins (H-K) compared to controls. This effect was even more pronounced in livers perfused with siRNA at 4° C. for 4 hours (L-O). Nuclei were visualized in cyan with DAPI, FAS siRNA in yellow with an AlexaFluor-555 3' modification, and cell membranes in red with wheat germ agglutinin conjugated to AlexaFluor-488 (ThermoFisher).

Thus, FIG. 8 shows for the first time that siRNA against the FAS receptor added directly to perfusion solution was uptaken into rat livers during hypothermic (4° C.) and normothermic (37° C.) perfusion. This data shows that silencing FAS during the ischemic period before transplantation can reduce and/or reverses graft damage.

While the invention is illustrated using exemplary embodiments, the invention is not limited to these illustrative embodiment, but rather contemplates combining, removing, and/or substituting features from different embodiments.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

REFERENCES

1. Neff G W, Duncan C W, Schiff E R. The current economic burden of cirrhosis. Gastroenterol Hepatol (N Y). 2011 October; 7(10):661-71.
2. Maximiliaan Thijssen, Carolina Moore, Xiaofei E, Xiaofei Wang, Pranoti Mandrekar, Adel Bozorgzadeh, Robert J. Porte, Timothy Kowalik, Paulo Martins. Silencing p53 Pathway of Apoptosis Alleviates Ischemia-Reperfusion Injury (IRI) in the Liver. Journal of the American College of Surgeons 225(4):e167 October 2017. DOI 10.1016/j.jamcollsurg.2017.07.979. Presented at the American College of Surgeons Meeting 2017, Oct. 22-26$^{th}$. San Diego. Selected as, Poster of exceptional Merit
3. Bradley S P, Rastellini C, da Costa M A, Kovalik T F, Bloomenthal A B, Brown M, Cicalese L, Basadonna G P, Uknis M E. Gene silencing in the endocrine pancreas mediated by short-interfering RNA. Pancreas, 2005 November; 31(4373-9.
4. Bradley S P, Kowalik T F, Rastellini C, da Costa M A, Bloomenthal A B, Cicalese L, Basadonna G P, Uknis M E. Successful incorporation of short-interfering RNA into islet cells by in situ perfusion. Transplant Proc. 2005 January-February; 37(1):233-6,
5. UNOS. Accessed September 2017
6. Pratschke J, Tullius S G, Neuhaus P. Brain death associated ischemia/reperfusion injury. Ann transplant 2004; 9:78-80.
7. Van der Woude F K. Graft immunogenicity revisited: Relevance of tissue-specific immunity, brain death and donor pretreatment. Nephron 2002; 91: 181-187.
8. Schuurs T A, Gerbens F, van der Hoeven J A et al. Distinct transcriptional changes in donor kidneys upon brain death induction in rats: insights in the process of brain death. Am J Transplant 2004; 4:1972-1981.
9. Medzhitov R, Janeway C A jr, Innate immunity: impact on the adaptive immune system. Curr Opn immunol 1997; 9: 4-7.
10. Tullius S G, Volk H D, Neuhaus P. Transplantation of organs from marginal donors. Transplantation 2001; 72: 1341-1349.
11. Johnson T D, Thacker L R, Jeon H, Lucas B A, Ranjan D. Sensitivity of expanded-criteria donor kidneys to cold ischaemia time. Clin transplant 2004; 18 (Suppl.12): 28-32.
12. Takeda K, Akira S. Toll-like receptors. Annu Rev Immunol 2003; 21: 335-376.
13. Geddes C C, Woo Y M, Jardine A. G. The impact of delayed graft function on the long-term outcome of renal transplantation. J Nephrol 2002; 15: 17-21.
14. Ojo A O, Wolfe R A, Held P J, Port F K, Schmouder R L. Delayed graft function: risk factors and implications for renal allograft survival. Transplantation 1997; 63: 968-974.
15. Leggat J E Jr, Ojo A O, Leichtman A B, et al. Long-term renal allograft survival: Prognostic implication of the timing of acute rejection episodes. Transplantation 1997; 63: 1268-1272.
16. Troppmann C, Gillingham K J, Benedetti E, et al. Delayed graft function, acute rejection, and outcome after cadaver renal transplantation: The multivariate analysis. Transplantation 1995; 59: 962-968.
17. Cosio F G, Pelletier R P, Falkenhain M E, et al. Impact of acute rejection and early allograft function on renal allograft survival. Transplantation 1997; 63: 1611-1615.
18. Koga 5, Toma H, Novick A C, Fairchild R L. Inibition of acute graft rejection in mice through neutralization of the chemokine Mig. Transplantation 1999; 67: 247-253.
19. Wood K J. Passenger leucocytes and microchimerism: what role in tolerance induction. Transplantation 2003; 75: 175-20S.

20. Matzinger P. The danger model: a renewed sense of self. Science 2002; 296: 301-305.
21. Game D S, Lechler R I. Pathways of allorecognition: implications for transplantation tolerance. Transplant Immunol 2002; 10: 101-108.
22. Hackstein H, Thomson A W. Dendritic cells: Emerging pharmacological targets of immunosuppressive drugs. Nat Rev Immunol 2004; 4: 24-34.
23. Takada M, Chandraker A, Ndeau. K C, Sayegh M, Tilney N L: The role of the B7 costimmulatory pathway in experimental cold ischemia/reperfusion injury. J Clin Invest 1997; 100: 1199-1203.
24. Karmann K, Hughes C C, Schechner J, Fanslow W C, Pober J S. CD40 on human endothelial cells: Inducibility by cytokines and functional regulation of adhesion molecule expression. Proc Natl Acad Sci USA 1995; 92: 4342-4364.
25. Raftery M J, Pearson T C. The relevance of induced class II HLA antigens and macrophage infiltration in early allograft biopsies. Transplantation 1989; 48: 238-243.
26. Rosendale J D, Chabalewski F L, McBride M A, et al. Increased transplanted organs from the use of a standardized donor management protocol. Am J Transplant 2002; 2: 761-768.
27. Valero R. Donor Management: One step forward. Am J Transplant 2002; 2: 693-694.
28. Lee Y K, Manalo D, Liu A Y. Heat shock response, heat shock transcription factor and cell aging. Biol Signals 1996; 5:180-191
29. Van der Woude F K. Graft immunogenicity revisited: Relevance of tissue-specific immunity, brain death and donor pretreatment. Nephron 2002; 91: 181-187.
30. Wheeldon D R, Potter C D, Oduro A, Wallwork J, Large S R. Transforming the unacceptable donor: outcomes from the adoption of a standardized donor management technique. J Heart Lung Transplant 1995: 14: 734-742.
31. Valero R. Donor Management: One step forward. Am J Transplant 2002; 2: 693-694.
32. Lee YK, Manalo D, Liu AY. Heat shock response, heat shock transcription factor and cell aging. Biol Signals 1996; 5:180-191.
33. Biguzas M, Jablonski P, Howden B O, et al. Evaluation of UW solution in rat kidney preservation. Transplantation 1990; 49: 1051-1055.
34. Brasile L, Stubenitsky B, Booster M, Arenada D, Haisch C, Kootstra G. Transfection and transgene expression in a human kidney during ex vivo warm perfusion. Transplant Proc 2002; 34: 2624.
35. Southard J H. Organ preservation. Annu Rev Med 1995; 46: 235-247.
36. Pratschke J, Wilhelm M J, Kusaka, Tilney N L. Accelerated rejection of renal allografts from brain dead donors. Ann Surg 2000; 232: 263-271.
37. Porter K A: Renal Transplantation, In Pathology of the kidney, edited by Heptinstall R H, Boston, Little, Brown&Co., 1992, p 1799-1934.
38. Mackersie R C, Bronster O L, Shackford S R. Organ procurement in patients with fatal head injuries. The fate of the potential donor. Ann Surg 1991; 213: 143-150.
39. Terasaki P I, Cecka M J, Gjertson D W, Takemoto S. High survival rates of kidney transplants from spousal and living unrelated donors. N Engl J Med 1995; 333: 333-336.
40. Tullius S G, Volk H D, Neuhaus P. Transplantation of organs from marginal donors. Transplantation 2001; 72: 1341-1349.
41. Fuhrman F A. The effect of body temperature on drug action. Physiol Rev. 1946 Apr;26:247-74.
42. Ballard B E, Ballard S S, Nelson E. Effect Of Temperature On Absorption Rates Of Drug Implants. J Pharm Sci. 1964 Apr; 53:424-8.
43. Ballard B E. Pharmacokinetics and temperature. J Pharm Sci. 1974 Sep;63(9):1345-58.
44. Akimoto J, Nakayama M, Okano T. Temperature-responsive polymeric micelles for optimizing drug targeting to solid tumors. J Control Release. 2014 Nov 10; 193:2-8.
45. Volpe D A, Shaw A B, Chen X H, Zhou L, Chen M L. Effect of altered temperature storage on the in vitro cellular uptake of liposome drug products. J Liposome Res. 2010 June; 20(2):178-82.
46. Magill R L, Niesman M R. Temperature-dependent drug release from large unilamellar liposomes. Cancer Drug Deliv. 1984;1(2):109-17.
47. Basak R, Bandyopadhyay R. Encapsulation of hydrophobic drugs in Pluronic F127 micelles: effects of drug hydrophobicity, solution temperature, and pH. Langmuir. 2013 Apr. 2; 29(13):4350-6.
48. Kowalik et al., U.S. Pat. No. 8,940,709, issued Jan. 27, 2015.
49. Ying Y 1, Kim J 2, Westphal S N 1, Long K E 1, Padanilam B J 3. Targeted deletion of p53 in the proximal tubule prevents ischemic renal injury. J Am Soc Nephroi. 2014 Dec; 25(12):2707-16. doi: 10.1681/ASN.2013121270. Epub 2014 May 22.

We claim:

1. A method for treating ischemia in a target tissue, comprising contacting the tissue, during ex vivo perfusion of the tissue, with a therapeutically effective amount of RNAi sequence that specifically binds to at least a portion of a gene that mediates ischemic injury in the tissue, thereby producing a treated tissue, wherein said RNAi comprises siRNA, wherein said siRNA comprises p53 gene siRNA, and wherein said p53 gene siRNA comprises an RNA sequence that specifically binds with mRNA encoded by p53 gene sequence 5'-GCATGAACCGAGGCCCAT-3' (SEQ ID NO: 1) or by the complement thereof.

2. The method of claim 1, wherein said p53 gene siRNA comprises one or both of p53 sense siRNA 5'-r(GCAUGAACCGAGGCCCAU)dTdT-3' (SEQ ID NO: 2) and p53 antisense 5'-r(AUGGGCCUCGGUUCAUGC)dTdT-3' (SEQ ID NO: 3).

3. The method of claim 1, wherein the target tissue comprises liver tissue.

4. The method of claim 1, wherein the contacting is prior to transplanting the treated tissue to a mammalian recipient.

5. The method of claim 4, wherein further comprising the step of transplanting the treated tissue into a transplant recipient.

6. The method of claim 1, wherein the ischemic injury comprises apoptosis.

7. The method of claim 1, wherein the ischemic injury comprises inflammation.

8. The method of claim 1, wherein the ischemic injury comprises neutrophil infiltration.

9. The method of claim 1, wherein said contacting comprises a normothermic temperature.

10. The method of claim 1, wherein said contacting comprises a hypothermic temperature.

11. The method of claim 1, wherein said contacting comprises a sub-normothermic temperature.

* * * * *